US010202651B2

(12) United States Patent
Lyons et al.

(10) Patent No.: US 10,202,651 B2
(45) Date of Patent: Feb. 12, 2019

(54) BIOMARKERS FOR INFLAMMATORY BOWEL DISEASE

(71) Applicant: Cambridge Enterprise Limited, Cambridge, Cambridgeshire (GB)

(72) Inventors: Paul A. Lyons, Cambridge (GB); Kenneth G. C. Smith, Cambridge (GB); Eoin F. McKinney, Cambridge (GB); Daniele Biasci, Cambridge (GB); James Lee, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 0 days.

(21) Appl. No.: 15/651,746

(22) Filed: Jul. 17, 2017

(65) Prior Publication Data

US 2018/0010189 A1 Jan. 11, 2018

Related U.S. Application Data

(63) Continuation of application No. 15/642,252, filed on Jul. 5, 2017.

(30) Foreign Application Priority Data

Jul. 5, 2016 (GB) .................................... 1611738.4

(51) Int. Cl.
C12Q 1/68 (2018.01)
C12Q 1/6883 (2018.01)
G06F 19/20 (2011.01)

(52) U.S. Cl.
CPC ........... *C12Q 1/6883* (2013.01); *G06F 19/20* (2013.01); *C12Q 2600/112* (2013.01); *C12Q 2600/118* (2013.01); *C12Q 2600/136* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2012/0289418 A1* 11/2012 Willard-Gallo ...... C12Q 1/6883
506/9
2013/0142809 A1* 6/2013 Welcher ................. G01N 33/68
424/145.1

2015/0133469 A1* 5/2015 O'Garra ................... C12Q 1/68
514/254.11
2015/0315643 A1* 11/2015 O'Garra ............... C12Q 1/6883
506/2
2017/0137885 A1* 5/2017 Salomon .............. C12Q 1/6883

FOREIGN PATENT DOCUMENTS

| WO | 2005/118851 | 12/2005 |
|----|-------------|---------|
| WO | 2010/084312 | 7/2010 |
| WO | 2016/066288 | 5/2016 |

OTHER PUBLICATIONS

Uchiumi et al. (Transcriptional Regulation of the Human Genes that Encode DNA Repair- and Mitochondrial Function-Associated Proteins, Ch. 5 in Biochemistry, Genetics and Molecular Biology, "Advances in DNA Repair," edited by Clark C. Chen, Published: Nov. 18, 2015).*
Tayari et al. (Long Noncoding RNA Expression Profiling in Normal B-Cell Subsets and Hodgkin Lymphoma Reveals Hodgkin and Reed-Sternberg Cell-Specific Long Noncoding RNAs, Am J Pathol. Sep. 2016;186(9):2462-72. Epub Jul. 14, 2016).*
International Searching Authority, International Search Report—International Application No. PCT/IB2017/000997, dated Jan. 16, 2018 together with the Written Opinion of the International Searching Authority, 13 pages.
Lee at al., "Gene expression profiling of CD8+ T cells predicts prognosis in patients with Crohn disease and ulcerative colitis," The Journal of Clinical Investigation, vol. 121, No. 10, pp. 4170-4179, Oct. 3, 2011.
McKinney et al., "A CD8+ T cell transcription signature predicts prognosis in autoimmune disease," Nature Medicine, vol. 16, No. 5, pp. 586-591, Apr. 18, 2010.

* cited by examiner

*Primary Examiner* — Aaron A Priest
(74) *Attorney, Agent, or Firm* — Nutter McClennen & Fish LLP

(57) ABSTRACT

The present invention provides a method of assessing whether an individual is at high risk or low risk of inflammatory bowel disease (IBD) progression by determining the expression level of two or more genes in a whole blood sample. Also provided are methods for treating IBD in an individual who is determined to be at high risk or low risk for IBD progression, and kits for assessing whether an individual is at high risk or low risk for IBD progression. Arrays, and methods of providing arrays, of patient-identified selected gene expression products from a whole blood sample of a patient are also provided.

20 Claims, 4 Drawing Sheets
Specification includes a Sequence Listing.

BIOMARKERS FOR INFLAMMATORY BOWEL DISEASE

CROSS-REFERENCE TO RELATED APPLICATIONS

The present application is a Continuation Application of U.S. patent application Ser. No. 15/642,252 filed Jul. 5, 2017, which claims priority to British patent application GB 1611738.4, filed Jul. 5, 2016, the contents of each of which are incorporated herein in their entirety.

FIELD OF THE INVENTION

The present invention relates to methods of assessing whether an individual is at high risk or low risk of inflammatory bowel disease (IBD) progression, including progression of Crohn's disease (CD) and ulcerative colitis (UC). The individual may optionally further be subjected to, or selected for, treatment for IBD, the treatment being selected on the basis of whether the individual is at high risk or low risk of IBD progression.

BACKGROUND TO THE INVENTION

It has been established that early introduction of aggressive therapies in CD leads to better outcomes, compared to the standard step-up approach (D'Haens et al., 2008; Colombel et al., 2010). In particular, patients treated with early combination therapy (infliximab in combination with Azathioprine; D'Haens et al., 2008) experience longer periods of steroid-free remission, are more likely to achieve mucosal healing and, ultimately, to avoid surgical resection (D'Haens et al., 2008; Colombel et al., 2010). However, this strategy is not suitable for all patients because a non-negligible proportion of patients would have achieved prolonged remission even with the conventional treatment approach (Jess et al., 2007), and thus their treatment with combination therapy would expose them to unnecessary side effects and toxicity. For this reason, the ability to predict prognosis would be a major step toward improving care for patients with CD, and IBD generally (IBD Research Priority, 2015; Gerich et al., 2014).

A number of different variables have been associated with prognosis in CD; namely clinical factors, serological markers, and genetic variants (Gerich et al., 2014; Billiet et al., 2014). However, the predictive power of these markers, used alone or in combination, has proven to be limited so far, and none are suitable for routine use in the clinic (Loly et al., 2008; Markowitz et al., 2011; Ananthakrishnan et al., 2014). As a consequence, developing a reliable prognostic test for IBD, including CD and UC, remains a priority, and is currently recognised as one of the most important unmet needs in gastroenterology (IBD Research Priority, 2015).

To accomplish this goal, genetic variants are promising candidate prognostic markers, because they are stable, can be easily measured, and because the genetic architecture of CD has already been studied extensively, at least with regard to susceptibility (Jostins et al., 2012). However, the genetic factors discovered so far may only explain 5-6% of the phenotypic variance observed in CD outcome between patients. Even if this figure were to increase, as better-powered studies discover other outcome-associated variants, it seems unlikely that genetic factors will be sufficient, in isolation, to enable accurate prediction of outcome in CD, and IBD generally. This is consistent with the notion that environmental factors, including smoking, play an important role in the natural history of IBD (Kaser et al., 2010).

Gene expression markers may be better candidates to overcome these limitations, particularly if measured directly in tissues or cell types which are involved in the disease pathogenesis (McKinney et al., 2010; Lee et al., 2011). In fact, gene expression may capture more information about interactions between organism and external environment (Choi et al., 2007), while still reflecting some aspects of individual genetic background. On the other hand, gene expression is not normally expected to be stable over time, and isolating particular cell populations without affecting gene expression levels is technically challenging (Lyons et al., 2007). Outside a controlled research environment, all of these factors limit the use of gene expression markers in a clinical context.

It has recently been reported that a distinctive gene expression signature, detectable in CD8+ T cells, can be used to predict prognosis in IBD (Lee et al., 2011). In particular, such a signature was able to identify, at the time of diagnosis and before therapy, two distinct groups of patients (IBD1 and IBD2), associated with different clinical courses in both CD and UC (Lee et al., 2011). More precisely, when managed with the standard step-up approach (Peyrin-Biroulet et al., 2008), patients classified as belonging to the IBD1 group consistently showed significantly higher risk of treatment escalation than patients in the IBD2 group (Lee et al., 2011), thus providing a rationale for treating these patients with more aggressive therapies at an earlier stage (Lee et al., 2011).

The aforementioned signature represented a major advance towards prediction of outcome in IBD (Friedman et al., 2011) for three main reasons. Firstly, the difference in outcome between patient strata is marked enough to be potentially useful to guide therapeutic decisions (Lee et al., 2011; Friedman et al., 2011), unlike previously reported prognostic markers (Gerich et al., 2014). Secondly, an overlapping CD8+ gene expression signature was previously reported to predict disease outcome in Systemic Lupus Erythematosus (SLE) and ANCA-associated vasculitis (AAV) patients, thus suggesting the hypothesis that common biological processes may underlie the prognosis of different inflammatory diseases (McKinney et al., 2010). Finally, a partial but compelling mechanistic explanation for the underlying biological processes was recently proposed (McKinney et al., 2015). These last two points are particularly important. In fact, investigating prognosis necessarily requires longitudinal studies where data collection is both time consuming and expensive, thus limiting the study size. As a consequence, it often remains in doubt whether a small cohort of patients can capture enough complexity from the underlying population and whether the proposed prognostic marker is indeed reproducible. In view of this, observing consistency with regard to disease outcomes across different cohorts of patients with different diseases, together with credible mechanistic insights, strongly increases the confidence in the reproducibility of the aforementioned CD8+ T cell gene expression signature (McKinney et al., 2010; Lee et al., 2011).

However, an important problem remains to be solved before the CD8+ T cell gene expression signature can be routinely used to stratify patients in a clinical setting. Assigning a patient to IBD1/IBD2 groups currently requires RNA extraction from purified CD8+ T cells (McKinney et al., 2010; Lee et al., 2011). It has been repeatedly observed that this step adds a considerable amount of complexity to a potential prognostic test, thus limiting its applicability to small numbers of samples in a controlled research setting (Friedman et al., 2011; Billiet et al., 2014).

On the contrary, being able to detect the IBD1/IBD2 subgroups in a readily accessible biological sample, such as whole blood, would greatly facilitate its clinical utility and, potentially, its applicability as a prognostic marker. Furthermore, because whole blood samples, but not purified CD8+ T cells, have been routinely collected during some clinical trials, this would open the possibility of reanalysing past IBD drug trials in order to re-evaluate drug efficacy after patient stratification.

Despite being potentially useful, it should be noted that detecting the IBD1/IBD2 signature in samples different from purified CD8+ T cells has previously proven to be challenging (Lee et al., 2011). In fact, it was repeatedly observed that gene expression signatures derived from CD4+ T cells could not be used to stratify patients by disease outcome in IBD (Lee et al., 2011), SLE, or AAV (McKinney et al., 2010). Consistent with these observations, it was not possible to identify equivalent prognostic signatures in peripheral blood mononuclear cells (PBMC) using the same unsupervised clustering methods (Monti et al., 2003) originally used to discover the CD8+ T cell expression signature (McKinney et al., 2010; Lee et al., 2011). This is may be due to the fact that CD8+ T cells represent a very small and variable fraction of the PBMC population (Lyons et al., 2007).

Moreover, while prognostic signatures can be discovered using high throughput gene expression profiling technologies, such as microarrays (Schena et al., 1995), a viable prognostic test needs to rely on a smaller scale gene expression platform such as real time quantitative PCR (RT-qPCR) (Freeman et al., 1999). In fact, most of modern prognostic tests developed for different conditions, such as AlloMap, Oncotype Dx and CorusCAD are qPCR based tests (Micheel et al., 2012), while only a few older tests, such as MammaPrint, rely on microarrays (Micheel et al., 2012). For this reason, if a signature that recapitulated the IBD1/IBD2 subgroups could be discovered in whole blood, the possibility of detecting it by qPCR would be crucial for its application in a clinical setting.

There thus remains a need in the art for an IBD1/IBD2 gene expression signature which can be detected in whole blood using methods such as qPCR.

Statements of Invention

The present inventors have surprisingly identified a gene expression signature that can be used to assess whether an individual is at high risk or low risk of IBD (e.g. ulcerative colitis or Crohn's disease) progression by analysing gene expression in a whole blood sample obtained from the individual. The expression of these genes in whole blood can be determined, for example, by RT-qPCR. Specifically, the present inventors have discovered that a high risk (IBD1) phenotype is characterised by upregulated expression of genes ARRDC4, GBP5, P2RY14, VTRNA1-1, IL18RAP, HP, NUDT7, GZMH, TRGC2, and GZMK, and downregulated expression of genes LGALSL, FCRL5, IF144L, LINC01136, LY96, and TRGV3 in whole blood, relative to the level of expression of these genes in an individual who has a low risk (IBD2) phenotype.

In one aspect, the present invention thus provides a method of assessing whether an individual is at high risk or low risk of IBD progression comprising establishing, by determining the expression level of two or more genes in a whole blood sample obtained from the individual, whether said individual has a high risk (IBD1) or low risk (IBD2) phenotype, wherein the two or more genes are selected from the group consisting of: ARRDC4, GBP5, P2RY14, VTRNA1-1, IL18RAP, HP, NUDT7, GZMH, TRGC2, LGALSL, FCRL5, IF144L, LINC01136, LY96, GZMK, and TRGV3.

In one embodiment, the method may comprise determining the expression level of said two or more genes using e.g. RT-qPCR, digital PCR, or whole transcriptome shotgun sequencing. In this case, the method may comprise: (i) providing a whole blood sample obtained from the individual; (ii) extracting RNA (e.g. mRNA) from the whole blood sample; (iii) converting the RNA (e.g. the mRNA) into cDNA, and (iv) performing RT-qPCR, digital PCR, or whole transcriptome shotgun sequencing to determine the expression level of the two or more genes.

The present invention also provides an autoimmune disease progression risk assessment system for use in a method of the invention, wherein the system comprises a tool or tools for determining the expression of two or more genes selected from the group consisting of: ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3, and a computer programmed to compute an IBD progression risk score from the gene expression data of the subject.

The tool(s) for determining expression of the genes may be, or comprise, reagents for establishing the expression level of the genes in question using any technique described herein, such as RT-qPCR, digital PCR, microarray analysis, whole transcriptome shotgun sequencing, or direct multiplexed gene expression analysis. For example, the tool(s) may be, or comprise, primers suitable for establishing the level of expression of the genes in question using e.g. RT-qPCR, digital PCR, whole transcriptome shotgun sequencing, or direct multiplexed gene expression analysis. The design of suitable primers is routine and well within the capabilities of the skilled person. Where the method comprises multiplexed gene expression analysis, the tool(s) may in addition, or alternatively, include fluorescent probes for establishing the level of expression of the genes in question. The tool(s) may also be, or comprise, RNA extraction reagents and/or reagents for reverse transcription of RNA into cDNA. The tool(s) may also be, or comprise, one or more articles and/or reagents for performance of the method, such as buffer solutions, and/or means for obtaining the test sample itself, e.g. means for obtaining and/or isolating a sample and sample handling containers (such components generally being sterile). The computation of an IBD progression risk score may be achieved in a number of ways and exemplary methods are set out below.

The present invention further provided is a method of treating IBD in an individual. In one embodiment, the method may comprise: (i) identifying the individual as one who is at high risk or low risk of IBD progression using a method of the invention, and (ii) subjecting the individual to treatment for IBD.

In an alternative embodiment, the method may comprise: (i) requesting a test providing the results of an analysis to determine the expression level of two or more genes in a whole blood sample obtained from the individual, wherein the two or more genes are selected from the group consisting of: ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3, and (ii) treating the individual determined to have an IBD1 or IBD2 phenotype for IBD.

Also provided is a kit for assessing whether an individual has a high risk IBD1 or low risk IBD2 phenotype, wherein said kit comprises reagents for establishing the expression level of two or more genes selected from the group consisting of: ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3.

The present invention also relates to an in vitro method of identifying a substance capable of inducing a low risk (IBD2) phenotype in an IBD patient. The method preferably comprises: providing (i) a whole blood sample obtained from an IBD patient prior to treatment with a substance of interest, and (ii) a whole blood sample obtained from the IBD patient following treatment with the substance of interest, wherein the IBD patient has been determined to have a high risk (IBD1) phenotype using a method of the invention; and determining the expression level of two or more genes selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3 in samples (i) and (ii); wherein a lower expression of genes ARRDC4, GBP5, P2RY14, VTRNA1-1, IL18RAP, HP, NUDT7, GZMH, TRGC2, and GZMK, and a higher expression of genes LGALSL, FCRL5, IF144L, LINC01136, LY96, and TRGV3 in sample (ii) relative to sample (i) indicates that the substance is capable of inducing a low risk (IBD2) phenotype in an IBD patient.

The present invention further relates to an in vitro method of identifying a substance capable of treating IBD in an individual. The method preferably comprises: (i) identifying an individual who is at high risk or low risk of IBD progression using a method of the invention; and (ii) comparing the level of IBD progression in the individual following treatment with the substance of interest with a control, wherein a lower level of IBD progression in the individual compared with the control indicates that the substance is capable of treating IBD.

DETAILED DESCRIPTION OF THE INVENTION

Figure 1:
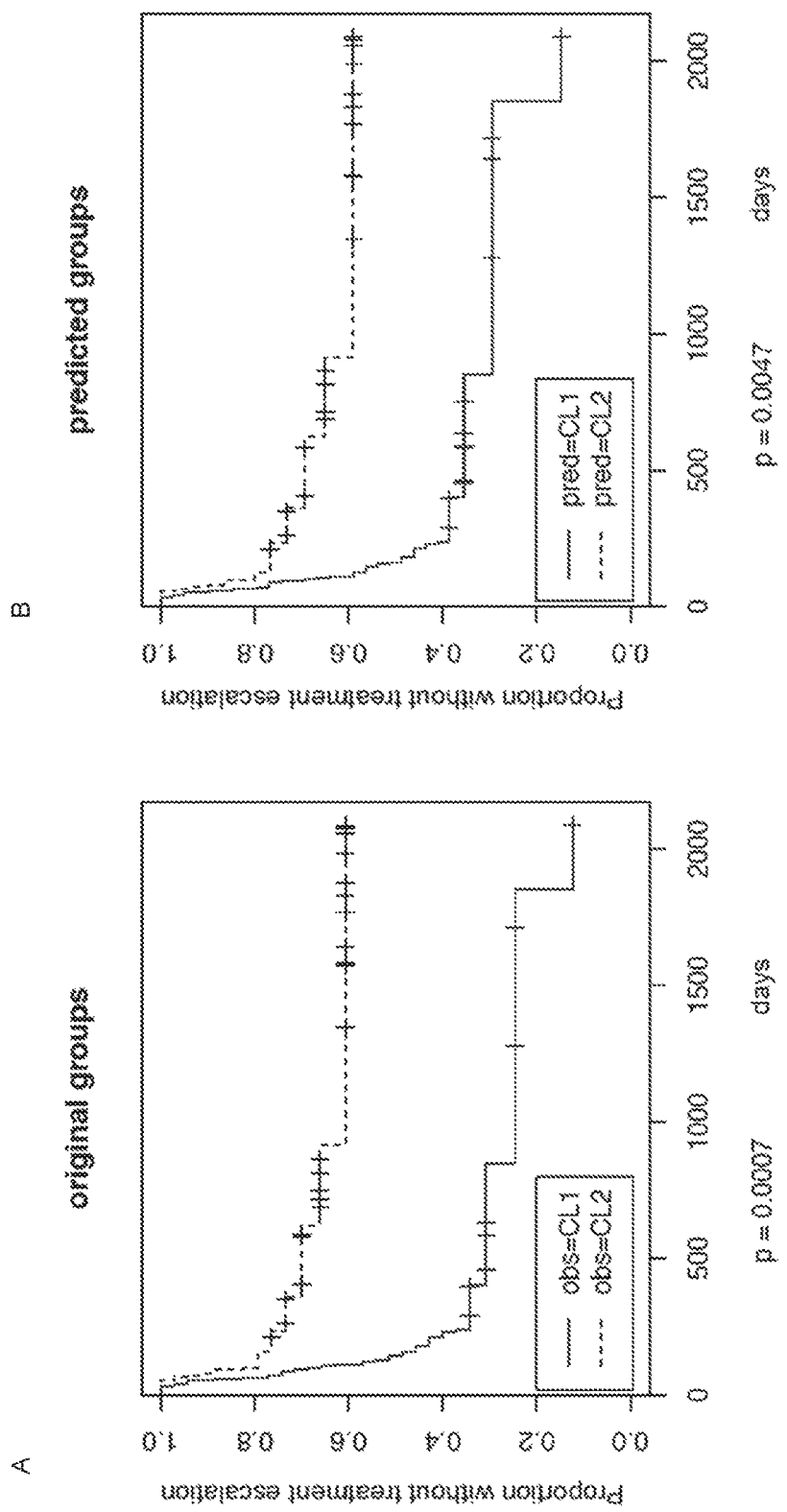
FIG. 1 shows a Kaplan-Meier plot comparing treatment escalation-free survival between the original CD8 T-cell based IBD1/IBD2 groups (left) and the IBD1/IBD2 groups predicted using the whole blood qPCR classifier described in Example 1 (right; see Table 1 for detail of genes included in classifier). Obs: observed original groups; pred: groups predicted using whole blood qPCR data; p: Log-rank test p-value. CL1 and CL2 refer to the IBD1 (high risk) and IBD2 (low risk) subgroups, respectively.

As mentioned above, the present inventors have identified a gene expression signature that can be used to assess whether an individual is at high risk or low risk of IBD progression by analysing gene expression in a whole blood sample obtained from the individual, for example by real time quantitative PCR (RT-qPCR).

Specifically, the present inventors have discovered that a high risk (IBD1) phenotype is characterised by upregulated expression of genes ARRDC4, GBP5, P2RY14, VTRNA1-1, IL18RAP, HP, NUDT7, GZMH, TRGC2, and GZMK, and downregulated expression of genes LGALSL, FCRL5, IF144L, LINC01136, LY96, and TRGV3, relative to the level of expression of these genes in an individual who has a low risk (IBD2) phenotype. The NCBI accession numbers (as well as GI numbers) for these genes are set out in Table 2 below.

As explained above, while methods for assessing whether an individual has a high risk (IBD1) or low risk (IBD2) phenotype have been described previously, these methods cannot be applied directly to whole blood samples, but rather require the isolation of e.g. CD8 T cells from blood samples, thus severely limiting their clinical applicability. In contrast, the gene expression signature identified by the present inventors can be detected in whole blood samples, thus eliminating the need for isolating a particular cell type from the blood sample and vastly increasing the clinical utility of diagnostic methods employing this gene expression signature. In particular, avoiding the need to isolate a particular cell type prior to gene expression analysis reduces the technical complexity of the methods of the invention, as well as making said methods less time consuming and more cost effective to perform.

A method disclosed herein, such as a method of assessing whether an individual is at high risk or low risk of IBD progression, may thus comprise determining the expression level of two or more genes selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3. Genes ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3 represent the top 16 marker genes for determining the presence of a high risk (IBD1) or low risk (IBD2) phenotype in a whole blood sample obtained from an individual, as identified by the present inventors.

Determining the expression level of two or more of said genes is expected to be more robust than determining the expression level of only a single gene. For example, determining the expression level of two or more genes may allow the presence, or absence, of a high risk (IBD1) or low risk (IBD2) phenotype to be accurately determined even if the expression level of e.g. one gene cannot be determined, or is inaccurate.

For example, a method disclosed herein, may comprise determining the expression level of three or more, four or more, five or more, six or more, seven or more, eight or more, nine or more, ten or more, eleven or more, twelve or more, thirteen or more, fourteen or more, fifteen or more, or all sixteen genes selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3. Preferably, a method disclosed herein comprises determining the expression level of at least five of the genes selected from the group consisting of ARRDC4, GBP5, P2RY14, VTRNA1-1, IL18RAP, HP, NUDT7, GZMH, TRGC2, GZMK, LGALSL, FCRL5, IFI44L, LINC01136, LY96, and TRGV3.

In a preferred embodiment, a method as disclosed herein may comprise determining the expression level of IL18RAP and TRGC2. In this embodiment, the method may optionally further comprise determining the expression level of one or more, two or more, three or more, four or more, five or more, six or more, seven or more, eight or more, nine or more, ten or more, eleven or more, twelve or more, thirteen or more, or all fourteen genes selected from the group consisting of ARRDC4, GBP5, P2RY14, VTRNA1-1, HP, NUDT7, GZMH, GZMK, LGALSL, FCRL5, IFI44L, LINC01136, LY96, and TRGV3.

In a further preferred embodiment, a method as disclosed herein may comprise determining the expression level of IL18RAP, TRGC2 and TRGV3. In this embodiment, the method may optionally further comprise determining the expression level of one or more, two or more, three or more, four or more, five or more, six or more, seven or more, eight or more, nine or more, ten or more, eleven or more, twelve or more, or all thirteen genes selected from the group consisting of ARRDC4, GBP5, P2RY14, VTRNA1-1, HP, NUDT7, GZMH, GZMK, LGALSL, FCRL5, IFI44L, LINC01136, and LY96.

In one aspect, the invention concerns a method of assessing whether an individual is at high risk or low risk of inflammatory bowel disease (IBD) progression, the method comprising establishing, by determining the expression level of two or more genes in a whole blood sample obtained from the individual, whether the individual has a high risk (IBD1) or low risk (IBD2) phenotype, wherein the two or more genes are selected from the group consisting of ARRDC4, GBP5, P2RY14, VTRNA1-1, IL18RAP, HP, NUDT7, GZMH TRGC2, GZMK, LGALSL, FCRL5, IFI44L, LINC01136, LY96, and TRGV3. The method of the invention may further comprise characterisation of an IBD1 phenotype by the upregulated expression of genes ARRDC4, GBP5, P2RY14, VTRNA1-1, IL18RAP, HP, NUDT7, GZMH, TRGC2, and GZMK, and downregulated expression of genes LGALSL, FCRL5, IFI44L, LINC01136, LY96, and TRGV3, relative to the level of expression of these genes in an individual who has an IBD2 phenotype. The method of the invention may further comprise determining the risk of progression of IBD in the individual by calculating a risk score for the patient by a) weighting the measured expression levels of the selected genes; b) applying a logistic regression model to the weighted expression levels to determine the risk score, wherein a risk score of less than 0.5 is indicative of low risk of IBD progression and a risk score of greater than 0.5 is indicative of high risk of IBD progression; and c) creating a report summarizing the result of the determination.

In certain aspects of the invention, the method may comprise selecting an individual identified as one who is at high risk or low risk of IBD progression for treatment for IBD. The method of the invention may further comprise subjecting an individual identified as one who is at high risk or low risk of IBD progression to treatment for IBD.

In certain aspects of the invention, the expression level of the two or more genes is determined using real time quantitative PCR (RT-qPCR), digital PCR, microarray analysis, whole transcriptome shotgun sequencing, or direct multiplexed gene expression analysis.

In certain aspects of the invention, the method comprises: (i) providing a whole blood sample obtained from the individual; (ii) extracting RNA from the whole blood sample; (iii) converting the RNA into cDNA; and (iv) performing RT-qPCR, digital PCR, or whole transcriptome shotgun sequencing to determine the expression level of the two or more genes.

In certain aspects, the invention concerns a method for treating IBD in an individual, the method comprising (i) identifying the individual as one who is at high risk or low risk of IBD progression and (ii) subjecting the individual to treatment for IBD.

Other aspects of the invention include an autoimmune disease progression risk assessment system for use in the method of the invention, the system comprising a tool or tools for determining the expression of two or more genes selected from the group consisting of: ARRDC4, GBP5, P2RY14, VTRNA1-1, IL18RAP, HP, NUDT7, GZMH, TRGC2, GZMK, LGALSL, FCRL5, IFI44L, LINC01136, LY96, and TRGV3, and a computer programmed to compute an IBD progression risk score from the gene expression data of the subject. The system may comprise a tool or tools for determining the expression of two or more genes by RT-qPCR, digital PCR, microarray analysis, whole transcriptome shotgun sequencing, or direct multiplexed gene expression analysis.

In certain aspects, the invention concerns a method for treating IBD in an individual who is determined to be at high risk or low risk for IBD progression, the method comprising (i) reviewing test results that classify said individual as IBD1 (high risk of IBD progression) or IBD2 (low risk of IBD progression), wherein the test determines expression levels of two or more genes, wherein the two or more genes are selected from the group consisting of ARRDC4, GBP5, P2RY14, VTRNA1-1, IL18RAP, HP, NUDT7, GZMH, TRGC2, GZMK, LGALSL, FCRL5, IFI44L, LINC01136, LY96, and TRGV3, in a whole blood sample obtained from the individual, and wherein upregulated expression of genes ARRDC4, GBP5, P2RY14, VTRNA1-1, IL18RAP, HP, NUDT7, GZMH, TRGC2, and GZMK, and downregulated expression of genes LGALSL, FCRL5, IFI44L, LINC01136, LY96, and TRGV3 relative to the level of expression of these genes in an individual who has a low risk (IBD2) phenotype, indicates that the individual has a high risk (IBD1) phenotype, and wherein downregulated expression of genes ARRDC4, GBP5, P2RY14, VTRNA1-1, IL18RAP, HP, NUDT7, GZMH, TRGC2, and GZMK, and upregulated expression of genes LGALSL, FCRL5, IFI44L, LINC01136, LY96, and TRGV3 relative to the level of expression of these genes in an individual who has a high risk (IBD1) phenotype, indicates that the individual has a low risk (IBD2) phenotype, and (ii) treating the individual determined to have an IBD1 or IBD2 phenotype for IBD. The method may further comprise requesting a test providing the results of an analysis to determine the expression level of two or more genes by RT-qPCR, digital PCR, microarray analysis, whole transcriptome shotgun sequencing, or direct multiplexed gene expression analysis.

In certain aspects, the invention concerns a kit for assessing whether an individual has a high risk IBD1 or low risk IBD2 phenotype, wherein the kit comprises reagents for establishing the expression level of two or more genes selected from the group consisting of: ARRDC4, GBP5, P2RY14, VTRNA1-1, IL18RAP, HP, NUDT7, GZMH, TRGC2, GZMK, LGALSL, FCRL5, IFI44L, LINC01136, LY96, and TRGV3, wherein an IBD1 phenotype is characterised by upregulated expression of genes ARRDC4, GBP5, P2RY14, VTRNA1-1, IL18RAP, HP, NUDT7, GZMH, TRGC2, and GZMK, and downregulated expression of genes LGALSL, FCRL5, IF144L, LINC01136, LY96, and TRGV3, relative to the level of expression of these genes in an individual who has an IBD2 phenotype, and wherein an IBD2 phenotype is characterised by downregulated expression of genes ARRDC4, GBP5, P2RY14, VTRNA1-1, IL18RAP, HP, NUDT7, GZMH, TRGC2, and GZMK, and upregulated expression of genes LGALSL, FCRL5, IF144L, LINC01136, LY96, and TRGV3 relative to the level of expression of these genes in an individual who has an IBD1 phenotype. The kit may comprise reagents for establishing the expression level of the two or more genes by RT-qPCR, microarray analysis, digital PCR, whole transcriptome shotgun sequencing, or direct multiplexed gene expression analysis.

In certain aspects of invention, IBD is ulcerative colitis (UC) or Crohn's disease.

In certain aspects, the invention concerns an in vitro method of identifying a substance capable of inducing a low risk (IBD2) phenotype in an IBD patient, the method comprising providing (i) a whole blood sample obtained from an IBD patient prior to treatment with a substance of interest, and (ii) a whole blood sample obtained from the IBD patient following treatment with the substance of interest, wherein the IBD patient has been determined to have a high risk (IBD1) phenotype; and determining the expression level of two or more genes selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3 in samples (i) and (ii); wherein a lower expression of genes ARRDC4, GBP5, P2RY14, VTRNA1-1, IL18RAP, HP, NUDT7, GZMH, TRGC2, and GZMK, and a higher expression of genes LGALSL, FCRL5, IF144L, LINC01136, LY96, and TRGV3 in sample (ii) relative to sample (i) indicates that the substance is capable of inducing a low risk (IBD2) phenotype in an IBD patient. The method may further comprise formulating a substance identified as capable of inducing a low risk (IBD2) phenotype in an IBD patient into a medicament.

In certain aspects, the invention concerns an in vitro method of identifying a substance capable of treating IBD in an individual, the method comprising (i) identifying an individual who is at high risk or low risk of IBD progression; and (ii) comparing the level of IBD progression in the individual following treatment with the substance of interest with a control, wherein a lower level of IBD progression in the individual compared with the control indicates that the substance is capable of treating IBD. The method may further comprise further comprise formulating a substance identified as capable of treating IBD into a medicament.

In certain aspects, the invention concerns a method of providing an array of patient-identified selected gene expression products from a whole blood sample of a patient, the method comprising a) providing RNA from a whole blood sample of said patient; b) converting the RNA into cDNA; c) placing individual aliquots of the cDNA on an array such that the cDNA aliquots are identified as patient sample cDNA aliquots; d) performing RT-qPCR, digital PCR, or whole transcriptome shotgun sequencing on the individual cDNA aliquots for each gene of three or more genes selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3 so as to provide RT-qPCR, digital PCR or whole transcriptome shotgun sequencing products on the array, thereby providing an array of patient-identified selected gene expression products consisting essentially of the three or more gene expression products. The method may further comprise the step of the step of quantifying the RT-qPCR, digital PCR or whole transcriptome shotgun sequencing products. RT-qPCR product may be provided provided by contacting the cDNA with a primer set specific for each of the three or more genes. The primer set may comprise a forward primer, a reverse primer, and a probe primer. In some embodiments, four, five, thirteen, fourteen, or sixteen of the genes are selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3.

In certain aspects, the invention concerns an array of patient-identified selected gene expression products from a whole blood sample of a patient, said array comprising individual cDNA aliquots identified as patient sample cDNA, wherein each of three or more cDNA aliquots of the array comprises an RT-qPCR primer pair specific to amplify in the cDNA aliquot a selected gene expression product, wherein the array comprises primer pairs specific for three or more genes selected from the group consisting of: ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3. The array may further comprise an RT-qPCR probe specific for the three or more of the genes. In some embodiments, four, five, thirteen, fourteen, or sixteen of the genes are selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3.

In certain aspects, the invention concerns a method of providing an array of quantified patient-identified selected gene expression products from a whole blood sample of a patient, the method comprising a) providing RNA from a whole blood sample of the patient; b) converting said RNA into cDNA; c) placing aliquots of said cDNA on an array such that the cDNA aliquots are identified as patient sample cDNA aliquots; and d) performing RT-qPCR, digital PCR, or whole transcriptome shotgun sequencing on said cDNA aliquots so as to provide RT-qPCR, digital PCR or whole transcriptome shotgun sequencing gene expression products on the array; and e) quantifying the amount of a gene expression product for each selected gene of three or more genes selected from the group of genes consisting of: ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3; thereby providing an array of quantified patient-identified selected gene expression products from a whole blood sample of a patient. In certain aspects of the method, for each selected gene expression product on the array, the amount of gene expression product for a gene selected from the group consisting of: ARRDC4, GBP5, P2RY14, VTRNA1-1, IL18RAP, HP, NUDT7, GZMH, TRGC2, and GZMK, is lower than a control for the gene; and the amount of gene expression product for a gene selected from the group consisting of: LGALSL, FCRL5, IF144L, LINC01136, LY96, and TRGV3 is higher than a control for the gene. In another aspect of the method, for each selected gene expression product on the array the amount of gene product for a gene selected from the group consisting of ARRDC4, GBP5, P2RY14, VTRNA1-1, IL18RAP, HP, NUDT7, GZMH, TRGC2, and GZMK, is higher than a control for the gene; and the amount of gene product for a gene selected from the group consisting of:

LGALSL, FCRL5, IF144L, LINC01136, LY96, and TRGV3 is lower than a control for the gene. In some embodiments, four, five, thirteen, fourteen, or sixteen of the genes are selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3.

In certain aspects, the invention concerns an array of quantified patient-identified selected gene expression products, the array comprising individual quantified gene expression products of a whole blood sample of a patient, the quantified gene expression products consisting of amplified cDNA products of three or more genes selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3. In some embodiments, for each selected gene expression product on the array, the amount of gene expression product for a gene selected from the group consisting of ARRDC4, GBP5, P2RY14, VTRNA1-1, IL18RAP, HP, NUDT7, GZMH, TRGC2, and GZMK, is lower than a control for the gene; and the amount of gene expression product for a gene selected from the group consisting of: LGALSL, FCRL5, IF144L, LINC01136, LY96, and TRGV3 is higher than a control for the gene. In some embodiments, the amount of gene product for a gene selected from the group consisting of ARRDC4, GBP5, P2RY14, VTRNA1-1, IL18RAP, HP, NUDT7, GZMH, TRGC2, and GZMK, is higher than a control for the gene; and the amount of gene product for a gene selected from the group consisting of: LGALSL, FCRL5, IFI44L, LINC01136, LY96, and TRGV3 is lower than a control for the gene. In some embodiments, four, five, thirteen, fourteen, or sixteen of the genes are selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3.

As used herein, the term "array" or "panel" is defined to mean a pool of nucleic acid molecules that is contained within or affixed to a one or more receptacles, substrates, or solid supports in a manner that permits the identification and quantitation of individual nucleic acid members during the course of experimental manipulation. Non-limiting examples of receptacles, substrates, or solid supports include a series of reactions tubes, microarrays, multi-well plates (e.g., 16-well, 32-well, 48-well, 96-well, 384-well, and 1536-well plates), microfluidic devices, and other receptacles, substrates, or solid supports well known in the art.

As used herein, "patient-identified" is defined to mean marked, labeled, coded, or otherwise indicated to have come from, originated from, or derived from an individual patient. Non-limiting examples include the patient's name, the patient's social security number, a barcode, a patient number, a code, a symbol, or other suitable unique identifiers.

As used herein, "gene expression product" is defined to mean a nucleic acid produced from the transcription of a particular gene. Non-limiting examples of a gene expression product include mRNA transcripts, cDNA and cDNA fragments created or derived from said mRNA, DNA or DNA fragments created from or derived from said mRNA or said cDNA and cDNA fragments. Non-limiting examples of gene expression products include mRNA, cDNA and cDNA fragments thereof created from said mRNA via reverse transcription, and DNA created or derived from said mRNA, cDNA, or cDNA fragments thereof produced via amplification using polymerase chain reaction (PCR), ligase chain reaction (LCR), and other nucleic acid amplification techniques well known in the art.

As used herein, "consisting essentially of" is defined as meaning optionally comprising -other elements or products that do not materially affect the result, outcome, or read-out of the claimed method, assay, or product.

As used herein, "quantified" is defined as meaning a determined amount of a gene expression product of a sample obtained from a patient. Non-limiting suitable methods of determining an amount of a gene expression product present in a sample derived from or obtained from a patient include RT-qPCR, digital PCR, whole transcriptome shotgun sequencing, direct multiplexed gene expression analysis, and other methods well known in the art.

As used herein, "primer pair" is defined as meaning two primers or oligonucleotides consisting of a forward and reverse primer or oligonucleotide, which are capable of amplifying a specific cDNA or DNA sequences, or fragments thereof via the polymerase chain reaction (PCR).

As used herein, "primer set" is defined as meaning one or more primer pairs that are capable of amplifying one or more specific cDNA or DNA sequences, or fragments thereof, via PCR.

As used herein, a "severe disease course" is defined as meaning the presentation of an IBD patient with relatively short periods between IBD flares and/or an increased rate of IBD disease flares over time. IBD flares are characterized by a Harvey Bradshaw (disease activity) index>5; and (i) a C Reactive Protein (CRP) level of >10 mg/l, (ii) a calprotectin level of >200 µg/g, or (iii) endoscopic evidence of disease activity.

As used herein, a "mild disease course" is defined as meaning the presentation of an IBD patient with relatively long periods between IBD flares and/or a rate of IBD disease flares that do not increase over time. IBD flares are characterized by a Harvey Bradshaw (disease activity) index>5; and (i) a C Reactive Protein (CRP) level of >10 mg/l, (ii) a calprotectin level of >200 µg/g, or (iii) endoscopic evidence of disease activity.

An individual who has high risk (IBD1) phenotype, and thus is at high risk of IBD progression, is characterised by upregulated expression of genes ARRDC4, GBP5, P2RY14, VTRNA1-1, IL18RAP, HP, NUDT7, GZMH, TRGC2, and GZMK, and downregulated expression of genes LGALSL, FCRL5, IF144L, LINC01136, LY96, and TRGV3, relative to the level of expression of these genes in an individual who has a low risk IBD2 phenotype.

Similarly, an individual who has low risk (IBD2) phenotype, and thus is at low risk of IBD progression, is characterised by downregulated expression of genes ARRDC4, GBP5, P2RY14, VTRNA1-1, IL18RAP, HP, NUDT7, GZMH, TRGC2, and GZMK, and upregulated expression of genes LGALSL, FCRL5, IF144L, LINC01136, LY96, and TRGV3, relative to the level of expression of these genes in an individual who has a high risk IBD1 phenotype.

An upregulated or downregulated expression of a gene may refer to a significantly upregulated, or significantly downregulated, level of expression of said gene, respectively. Whether an individual has an upregulated or downregulated level of expression of the genes in question may be determined by any convenient means and many suitable techniques are known in the art and described herein.

As is the case with most biomarkers, accuracy of prediction may not be absolute. Individuals are thus classed as being either at high risk or low risk of IBD progression. This risk may expressed in a number of ways.

For example, whether an individual is at high risk or low risk of IBD progression may be expressed in terms of a hazard rate. The hazard rate here describes the instantaneous probability of IBD progression in an individual who has a high risk (IBD1) or low risk (IBD2) phenotype. Alternatively, the risk of IBD progression may be expressed in terms of a hazard ratio (HR), where the hazard ratio describes the probability of IBD progression occurring in an individual who has a high risk (IBD1) phenotype relative to an individual who has a low risk (IBD2) phenotype.

Figure 3:
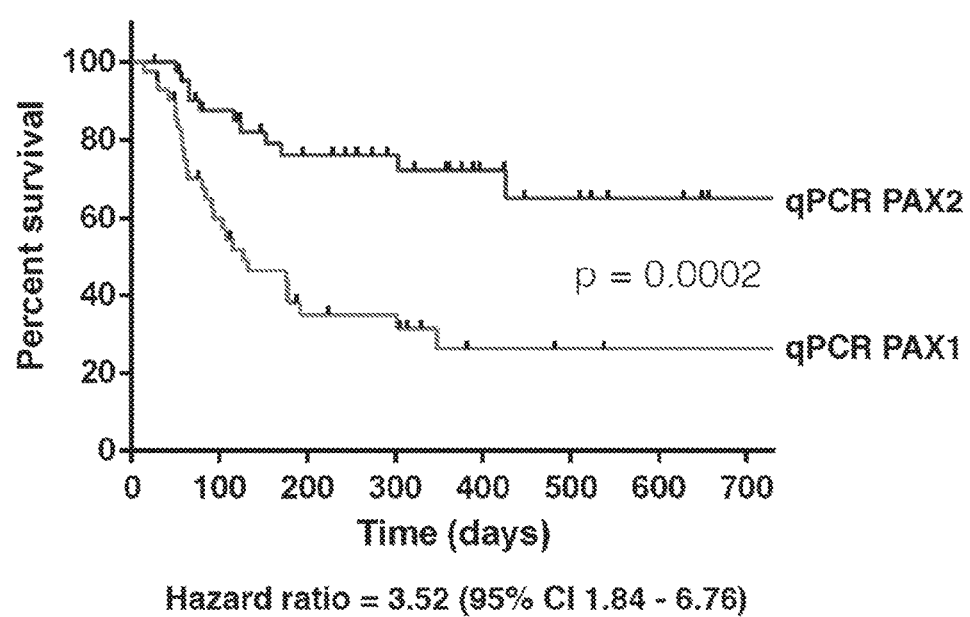
FIG. 3 shows a Kaplan-Meier plot showing treatment escalation-free survival in the IBD1/IBD2 groups predicted using the optimised whole blood qPCR classifier described in Example 2 in an independent cohort of 85 newly diagnosed IBD patients (see Table 2 for detail of genes included in classifier). qPCR PAX1 and qPCR PAX2 refer to subgroups IBD1 and IBD2, respectively. The hazard ratio for subgroup IBD1 relative to subgroup IBD2 was 3.52, as indicated in FIG. 3.

The present inventors have shown that individuals who had a high risk (IBD1) phenotype had a hazard ratio of 3.52 with regard to the probability of IBD progression relative to individuals who had a low risk (IBD2) phenotype (see Example 3 and FIG. 3).

In a preferred embodiment, an individual who is at high risk of IBD progression may thus have a hazard rate with regard to IBD progression which is at least 2, at least 2.5, at least 3, or at least 3.5 times higher than the hazard rate of an individual who is at low risk of IBD progression. Similarly, an individual who is at low risk of IBD progression may have a hazard rate with regard to IBD progression which is at least 2, at least 2.5, at least 3, or at least 3.5 times lower than the hazard rate of an individual who is at high risk of IBD progression. Thus, an individual who is at high risk of IBD progression, may have a hazard ratio with regard to IBD progression of at least 2, at least 2.5, at least 3, or at least 3.5 relative to an individual who is at low risk of IBD progression. More preferably, an individual who is at high risk of IBD progression, has a hazard rate with regard to IBD progression which is at least 3.5 times higher than the hazard rate of an individual who is at low risk of IBD progression, i.e. has a hazard ratio with regard to IBD progression of at least 3.5 relative to an individual who is at low risk of IBD progression, and an individual who is at low risk of IBD progression, has a hazard rate with regard to IBD progression which is at least 3.5 times lower than the hazard rate of an individual who is at high risk of IBD progression.

Alternatively, an individual who is at high risk of IBD progression, may be at least 1.1 times, at least 1.2 times, at least 1.3 times, at least 1.4 times, at least 1.5 times, at least 1.6 times, at least 1.7 times, at least 1.8 times, at least 1.9 times, at least 2 times, at least 2.1 times, at least 2.2 times, at least 2.3 times, at least 2.4 times, at least 2.5 times, at least 2.6 times, at least 2.7 times, at least 2.8 times, at least 2.9 times, at least 3 times, at least 3.1 times, at least 3.2 times, at least 3.3 times, at least 3.4 times, or at least 3.5 times, more likely to experience IBD progression than an individual who is at low risk of IBD progression. Similarly, an individual who is at low risk of IBD progression, may be at least 1.1 times, at least 1.2 times, at least 1.3 times, at least 1.4 times, at least 1.5 times, at least 1.6 times, at least 1.7 times, at least 1.8 times, at least 1.9 times, at least 2 times, at least 2.1 times, at least 2.2 times, at least 2.3 times, at least 2.4 times, at least 2.5 times, at least 2.6 times, at least 2.7 times, at least 2.8 times, at least 2.9 times, at least 3 times, at least 3.1 times, at least 3.2 times, at least 3.3 times, at least 3.4 times, or at least 3.5 times, less likely to experience IBD progression than an individual who is at high risk of IBD progression. The likelihood of IBD progression may refer to the likelihood of IBD progression over a one year, two year, three year, four year or five year period.

Thus, an individual who is at high risk of IBD progression may have at least a 10%, at least a 20%, at least a 30%, at least a 40%, at least a 50%, at least a 60%, at least a 70%, at least a 80%, at least a 90%, at least a 100%, at least a 110%, at least a 120%, at least a 130%, at least a 140%, at least a 150%, at least a 160%, at least a 170%, at least a 180%, at least a 190%, at least a 200%, at least a 210%, at least a 220%, at least a 230%, at least a 240%, at least a 250%, at least a 260%, at least a 270%, at least a 280%, at least a 290%, at least a 300%, at least a 310%, at least a 320%, at least a 330%, at least a 340%, or at least a 350%, higher probability of IBD progression than an individual who is at low risk of IBD progression. Similarly, an individual who is at low risk of IBD progression may have at least a 10%, at least a 20%, at least a 30%, at least a 40%, at least a 50%, at least a 60%, at least a 70%, at least a 80%, at least a 90%, at least a 100%, at least a 110%, at least a 120%, at least a 130%, at least a 140%, at least a 150%, at least a 160%, at least a 170%, at least a 180%, at least a 190%, at least a 200%, at least a 210%, at least a 220%, at least a 230%, at least a 240%, at least a 250%, at least a 260%, at least a 270%, at least a 280%, at least a 290%, at least a 300%, at least a 310%, at least a 320%, at least a 330%, at least a 340%, or at least a 350%, lower probability of IBD progression than an individual who is at high risk of IBD progression. The probability of IBD progression may refer to the probability of IBD progression over a one year, two year, three year, four year or five year period.

There are many suitable methods which may be used to establish whether an individual has a high risk (IBD1) or low risk (IBD2) phenotype (also referred to herein as an IBD progression risk score), by determining the expression levels of two or more genes selected from the group consisting of: ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3 in a sample obtained from the individual (i.e. the test sample), wherein the sample is preferably a whole blood sample.

For example, the level of expression of two or more genes selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3 in a sample obtained from the individual may be compared to a collection of data that links expression of the genes in question to a high risk (IBD1) or low risk (IBD2) phenotype. In a preferred embodiment, the level of expression of two or more genes selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3 in a sample obtained from the individual is compared to expression data for the genes in question obtained from individuals known to have a high risk (IBD1) or low risk (IBD2) phenotype and, from said comparison, it is assessed whether the individual is at high risk or low risk of IBD progression. The comparison may use a linear regression model.

Alternatively, the level of expression of two or more genes selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3 in a sample obtained from the individual may be used to establish whether an individual has a high risk (IBD1) or low risk (IBD2) phenotype through use of a computational model based on gene expression data for the genes in question obtained from individuals known to have IBD and a suitable machine learning technique (such as logistic regression, support vector machines, or decision tree-based methods). For example, the computational model may be based on gene expression data for the genes in question obtained from individuals known to have a high risk (IBD1) or low risk (IBD2) phenotype. Alternatively, the computational model may be based on gene expression data for the genes in question obtained from individuals which are known to have IBD and which are known to have or to have not experienced IBD progression.

In a further example, the level of expression of two or more genes selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3 in a sample, which is preferably a whole blood sample obtained from an individual (i.e. the test sample), may be compared with a threshold level for each gene in question. A suitable threshold level for a gene can be determined, for example, using qPCR expression data and machine learning methods (such as logistic regression, support vector machines, or decision tree-based methods) to establish an optimal expression threshold that allows maximal separation of patients into the discrete prognostic subgroups IBD1 and IBD2. Comparison of the level of expression of two or more genes selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3 with a threshold level for each of the genes in question may thus indicate whether the individual has high risk (IBD1) or low risk (IBD2) phenotype.

Alternatively, the median expression level of each of the genes in question (i.e. two or more genes selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3) in samples obtained from a group of individuals may be used as a control value, wherein the group consisted of individuals, preferably at least 100, at least 50, or at least 10 individuals, who did not have IBD progression. In this case, an above median expression level of genes ARRDC4, GBP5, P2RY14, VTRNA1-1, IL18RAP, HP, NUDT7, GZMH, TRGC2, or GZMK, or a below median expression level of genes LGALSL, FCRL5, IF144L, LINC01136, LY96, or TRGV3 in a whole blood sample obtained from an individual may indicate the presence of a high risk (IBD1) phenotype, while an equal or below median expression level of genes ARRDC4, GBP5, P2RY14, VTRNA1-1, IL18RAP, HP, NUDT7, GZMH, TRGC2, or GZMK, or an equal or above median expression level of genes LGALSL, FCRL5, IF144L, LINC01136, LY96, or TRGV3 in a whole blood sample obtained from an individual may indicate presence of a low risk (IBD2) phenotype.

As a further alternative, the median expression level of each of the genes in question in samples obtained from a group of individuals, preferably at least 100, at least 50, or at least 10 individuals, may be used as a control, wherein the group consisted of individuals who had IBD progression. In this case, an equal or above median expression level of genes ARRDC4, GBP5, P2RY14, VTRNA1-1, IL18RAP, HP, NUDT7, GZMH, TRGC2, or GZMK, or an equal or below median expression level of genes LGALSL, FCRL5, IF144L, LINC01136, LY96, or TRGV3 in a whole blood sample obtained from an individual may indicate the presence of a high risk (IBD1) phenotype, while a below median expression level of genes ARRDC4, GBP5, P2RY14, VTRNA1-1, IL18RAP, HP, NUDT7, GZMH, TRGC2, or GZMK, or an above median expression level of genes LGALSL, FCRL5, IF144L, LINC01136, LY96, or TRGV3 in a whole blood sample obtained from an individual may indicate presence of a low risk (IBD2) phenotype.

As a yet further alternative, the median expression level of each of the genes in question in samples obtained from a group of individuals, preferably at least 100, at least 50, or at least 10 individual may be used as a control, wherein the group comprised individuals who did and did not have IBD progression. Preferably the group comprised an equal number, or essentially equal number, of individuals who did and did not have IBD progression. In this case, an above median expression level of genes ARRDC4, GBP5, P2RY14, VTRNA1-1, IL18RAP, HP, NUDT7, GZMH, TRGC2, or GZMK, or a below median expression level of genes LGALSL, FCRL5, IF144L, LINC01136, LY96, or TRGV3 in a whole blood sample obtained from the individual may indicate the presence of a high risk (IBD1) phenotype, while a below median expression level of genes ARRDC4, GBP5, P2RY14, VTRNA1-1, IL18RAP, HP, NUDT7, GZMH, TRGC2, or GZMK, or above median expression level of genes LGALSL, FCRL5, IF144L, LINC01136, LY96, or TRGV3 in a whole blood sample obtained from the individual may indicate presence of a low risk (IBD2) phenotype.

The level of expression of genes ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3 may be determined by any convenient means and many suitable techniques are known in the art. For example, suitable techniques include: real time quantitative PCR (RT-qPCR), digital PCR, microarray analysis, whole transcriptome shotgun sequencing (RNA-SEQ), direct multiplexed gene expression analysis, enzyme-linked immunosorbent assays (ELISA), protein chips, flow cytometry (such as Flow-FISH for RNA, also referred to as FlowRNA), mass spectrometry, Western blotting, and northern blotting. A method of the invention may therefore comprise bringing a whole blood sample obtained from an individual into contact with a reagent suitable for determining the expression level of two or more genes selected from the group of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3, e.g. a reagent or reagents suitable for determining the expression level of two or more of said genes using RT-qPCR, digital PCR, microarray analysis, whole transcriptome shotgun sequencing, direct multiplexed gene expression analysis, ELISA, protein chips, flow cytometry, mass spectrometry, or Western blotting. For example, the reagent may be a pair or pairs of nucleic acid primers, suitable for determining the expression level of one or more of said genes using RT-qPCR, digital PCR, or whole transcriptome shotgun sequencing. Alternatively, the reagent may be an antibody suitable for determining the expression level of said one or more genes using ELISA or Western blotting. Preferably, the level of expression of said genes is determined using RT-qPCR, digital PCR, microarray analysis, whole transcriptome shotgun sequencing, or direct multiplexed gene expression analysis. Most preferably, the level of expression of said genes is determined using RT-qPCR.

RT-qPCR allows amplification and simultaneous quantification of a target DNA molecule. To analyze gene expression levels using RT-qPCR, the total mRNA of a whole blood sample may first be isolated and reverse transcribed into cDNA using reverse transcriptase. For example, mRNA levels can be determined using e.g. Taqman Gene Expression Assays (Applied Biosystems) on an ABI PRISM 7900HT instrument according to the manufacturer's instructions. Transcript abundance can then be calculated by comparison to a standard curve.

Digital PCR is a new approach to nucleic acid detection and quantification that offers an alternate method to conventional real-time quantitative PCR for absolute quantification and rare allele detection. Digital PCR works by partitioning a sample of DNA or cDNA into many individual, parallel PCR reactions; some of these reactions contain the target molecule (positive) while others do not (negative). A single molecule can be amplified a million-fold or more. During amplification, TaqMan® chemistry with dye-labeled probes is used to detect sequence-specific targets. When no target sequence is present, no signal accumulates. Following PCR analysis, the fraction of negative reactions is used to generate an absolute count of the number of target molecules in the sample, without the need for standards or endogenous controls. The use of a nanofluidic chip provides a convenient and straightforward mechanism to run thousands of PCR reactions in parallel. Each well is loaded with a mixture of sample, master mix, and TaqMan® Assay reagents, and individually analyzed to detect the presence (positive) or absence (negative) of an endpoint signal. To account for wells that may have received more than one molecule of the target sequence, a correction factor is applied using the Poisson model.

RNA-SEQ uses next-generation sequencing (NGS) for the detection and quantification of RNA in a biological sample at a given moment in time. An RNA library is prepared, transcribed, fragmented, sequenced, reassembled and the sequence or sequences of interest quantified.

NanoString technology uses unique color-coded molecular barcodes that can hybridize directly to many different types of target nucleic acid molecules, and offers a cost-effective way to analyze the expression levels of up to 800 genes simultaneously, with sensitivity comparable to qPCR.

Flow-FISH for RNA employs flow cytometry to determine the abundance of a target mRNA within a sample using fluorescently-tagged RNA oligos. This technique is described, for example, in Porichis et al., Nat Comm (2014) 5:5641. The advantage of this technique is that it can be used without the need to separate the cells present in a sample.

Microarrays allow gene expression in two samples to be compared. Total RNA is first isolated from, e.g. PBMCs or whole blood using, for example, Trizol or an RNeasy mini kit (Qiagen). The isolated total RNA is then reverse transcribed into double-stranded cDNA using reverse transcriptase and polyT primers and labelled using e.g. Cy3- or Cy5-dCTP. Appropriate Cy3- and Cy5-labelled samples are then pooled and hybridised to custom spotted oligonucleotide microarrays comprised of probes representing suitable genes and control features, such as the microarray described in (Willcocks et al., J Exp Med 205, 1573-82, 2008). Samples may be hybridised in duplicate, using a dye-swap strategy, against a common reference RNA derived from pooled PBMC or whole blood samples. Following hybridisation, arrays are washed and scanned on e.g. an Agilent G2565B scanner. Suitable alternatives to the steps described above are well known in the art and would be apparent to the skilled person. The raw microarray data obtained can then be analyzed using suitable methods to determine the relative expression of genes ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3, as applicable.

Enzyme-linked immunosorbent assays (ELISAs) allow the relative amounts of proteins present in a sample to be detected. The sample is first immobilized on a solid support, such as a polystyrene microtiter plate, either directly or via an antibody specific for the protein of interest. After immobilization, the antigen is detected using an antibody specific for the target protein. Either the primary antibody used to detect the target protein may be labelled to allow detection, or the primary antibody can be detected using a suitably labelled secondary antibody. For example, the antibody may be labelled by conjugating the antibody to a reporter enzyme. In this case, the plate developed by adding a suitable enzymatic substrate to produce a visible signal. The intensity of the signal is dependent on the amount of target protein present in the sample.

Protein chips, also referred to as protein arrays or protein microarrays, allow the relative amounts of proteins present in a sample to be detected. Different capture molecules may be affixed to the chip. Examples include antibodies, antigens, enzymatic substrates, nucleotides and other proteins. Protein chips can also contain molecules that bind to a range of proteins. Protein chips are well known in the art and many different protein chips are commercially available.

Western blotting also allows the relative amounts of proteins present in a sample to be determined. The proteins present in a sample are first separated using gel electrophoresis. The proteins are then transferred to a membrane, e.g. a nitrocellulose or PVDF membrane, and detected using monoclonal or polyclonal antibodies specific to the target protein. Many different antibodies are commercially available and methods for making antibodies to a given target protein are also well established in the art. To allow detection, the antibodies specific for the protein(s) of interest, or suitable secondary antibodies, may, for example, be linked to a reporter enzyme, which drives a colorimetric reaction and produces a colour when exposed to an appropriate substrate. Other reporter enzymes include horseradish peroxidase, which produces chemiluminescence when provided with an appropriate substrate. Antibodies may also be labelled with suitable radioactive or fluorescent labels.

Depending on the label used, protein levels may be determined using densitometry, spectrophotometry, photographic film, X-ray film, or a photosensor.

Flow cytometry allows the relative amounts of proteins present in e.g. a PBMC or whole blood sample obtained from a subject to be determined. Flow cytometry can also be used to detect or measure the level of expression of a protein of interest on the surface of cells. Detection of proteins and cells using flow cytometry normally involves first attaching a fluorescent label to the protein or cell of interest. The fluorescent label may for example be a fluorescently-labelled antibody specific for the protein or cell of interest. Many different antibodies are commercially available and methods for making antibodies specific for a protein of interest are also well established in the art.

Mass spectrometry, e.g. matrix-assisted laser desorption/ ionization (MALDI) mass spectrometry, allows the identification of proteins present in a sample obtained from a individual using e.g. peptide mass finger printing. Prior to mass spectrometry the proteins present in the sample may be isolated using gel electrophoresis, e.g. SDS-PAGE, size exclusion chromatography, or two-dimensional gel electrophoresis.

Also disclosed is a kit for use in assessing whether an individual has a high risk (IBD1) or low risk (IBD2) phenotype, or for assessing whether a high risk (IBD1) or low risk (IBD2) phenotype is present in a whole blood sample obtained from an individual. The kit may comprise reagents for establishing the expression level of two or more genes selected from the group consisting of: ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3. The NCBI accession numbers (as well as GI numbers) for these genes are set out in Table 2. The kit may comprise reagents for establishing the expression level of three or more, four or more, five or more, six or more, seven or more, eight or more, nine or more, ten or more, eleven or more, twelve or more, thirteen or more, fourteen or more, fifteen or more, or all sixteen of the genes selected from the group consisting of: ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3. Preferably, the kit comprises reagents for establishing the expression level of at least five of the genes selected from the group consisting of: ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3.

In a preferred embodiment, the kit comprises reagents for establishing the expression level of IL18RAP and TRGC2, and optionally reagents for establishing the expression level of one or more, two or more, three or more, four or more, five or more, six or more, seven or more, eight or more, nine or more, ten or more, eleven or more, twelve or more, thirteen or more, or all fourteen genes selected from the group consisting of ARRDC4, GBP5, P2RY14, VTRNA1-1, HP, NUDT7, GZMH, GZMK, LGALSL, FCRL5, IF144L, LINC01136, LY96, and TRGV3.

In a further preferred embodiment, the kit comprises reagents for establishing the expression level of IL18RAP, TRGC2 and TRGV3, and optionally reagents for establishing the expression level of one or more, two or more, three or more, four or more, five or more, six or more, seven or more, eight or more, nine or more, ten or more, eleven or more, twelve or more, or all thirteen genes selected from the group consisting of ARRDC4, GBP5, P2RY14, VTRNA1-1, HP, NUDT7, GZMH, GZMK, LGALSL, FCRL5, IF144L, LINC01136, and LY96.

For example, the reagents may be reagents suitable for establishing the expression of the genes in question using any technique described herein, such as RT-qPCR, digital PCR, microarray analysis, whole transcriptome shotgun sequencing, or direct multiplexed gene expression analysis. For example, the kit may comprise primers suitable for establishing the level of expression of the genes in question using e.g. RT-qPCR, digital PCR, whole transcriptome shotgun sequencing, or direct multiplexed gene expression analysis. The design of suitable primers is routine and well within the capabilities of the skilled person. A kit for direct multiplexed gene expression analysis may in addition, or alternatively, include fluorescent probes for establishing the level of expression of the genes in question.

In addition to detection reagents, the kit may also include RNA extraction reagents and/or reagents for reverse transcription of RNA into cDNA.

A kit may also include one or more articles and/or reagents for performance of the method, such as buffer solutions, and/or means for obtaining the test sample itself, e.g. means for obtaining and/or isolating a sample and sample handling containers (such components generally being sterile). The kit may include instructions for use of the kit in a method for assessing whether an individual has a high risk (IBD1) or low risk (IBD2) phenotype, or whether high risk (IBD1) or low risk (IBD2) phenotype is present in a whole blood sample.

A major advantage of the present invention is that the expression level of the genes identified by the inventors can be determined in a whole blood sample obtained from an individual to assess whether the individual has a high risk (IBD1) or low risk (IBD2) phenotype. Thus, a sample as referred to in the context of the present invention is preferably a whole blood sample. The terms whole blood sample, peripheral blood sample, and peripheral whole blood sample are used interchangeably herein. A whole blood sample refers to a sample of blood, e.g. peripheral blood, obtained from an individual with all its components. The term "whole blood sample" as used herein therefore does not encompass a sample of (a) specific blood cell type(s) isolated from whole blood, such as isolated peripheral blood mononuclear cells (PBMCs) or isolated T cells, such as isolated CD8+ or CD4+ T cells, as employed in the methods of the prior art. The whole blood sample may be subjected to processing following sample collection, such as cell lysis and/or addition of one or more enzyme inhibitors to inhibit RNA degradation in the whole blood sample.

Although the present invention is directed to the a method of assessing whether an individual is at high risk or low risk of IBD progression by determining the expression level of two or more genes in a whole blood sample (rather than e.g. a PBMC sample) obtained from the individual, it is expected that determining the expression level of two or more genes selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3, in a PBMC sample obtained from an individual could similarly be used to assess whether the individual is at high risk or low risk of IBD progression. However, this is not claimed.

The term "individual" refers to a human individual. An individual may also be referred to as a patient, i.e. a human patient. In the context of the present invention, the individual has IBD unless the context dictates otherwise. Preferably the individual has been diagnosed with IBD. As IBD is characterised by periods of severe symptoms (flare-ups) and periods of remission, the individual may be experiencing a flare-up of IBD or be in remission from IBD.

IBD refers to a group of conditions characterised by inflammation of the gut. Symptoms of IBD can include abdominal pain, recurring or bloody diarrhoea, loss of appetite and weight loss, tiredness and fatigue, as well as anaemia. The two main types of IBD are ulcerative colitis (UC) and Crohn's disease (CD). Other types include collagenous colitis and lymphocytic colitis. UC and Crohn's disease affect more than 300.000 people in the UK alone. Ulcerative colitis primarily affects the colon and the rectum, whereas Crohn's disease affects the small intestine and large intestine, and can also affect the mouth, esophagus, stomach and the anus. UC and Crohn's disease are chronic conditions characterised by periods of severe symptoms (disease flare-ups) and periods of remission. There is no cure for either disease but treatments are available, including anti-inflammatory and immunosuppressive therapy, as well as surgery.

"IBD progression" refers to the progression of IBD after initial presentation of the disease in an individual. IBD, including UC and Crohn's disease, is characterised by relapses of the disease. These relapses are also referred to as flare-ups. Accordingly, IBD progression may refer to relapses, or flare-ups, of IBD after initial presentation of the disease. In particular, IBD progression may refer to a high frequency of relapses, or flare-ups, of IBD after initial presentation of the disease. The present inventors found that the individuals identified as belonging to the IBD1 and IBD2 subgroups in Example 3 respectively had an average of 0.66 and 0.34 relapses, or flare-ups, of IBD over a period of 12 months after initial presentation of the disease. A high frequency of relapses, or flare-ups, may therefore refer to an average of 0.5 or more, or 0.6 or more, preferably an average of 0.6 or more, relapses, or flare-ups, over a period of 12 months after initial presentation of the disease, or within 12 months of initial presentation of the disease. A relapse or flare-up may be an event that requires increased therapy, e.g. increased immunosuppressive or anti-inflammatory therapy or surgery. Such a requirement for increased therapy may also be referred to as treatment escalation. A relapse or flare-up may result in bowel damage or destruction if left untreated, or if inadequately treated. A high risk of IBD progression may accordingly refer to a high risk that the individual will experience relapses or flare-ups of the disease after initial presentation, in particular a high risk that the individual will experience on average 0.6 or more relapses or flare-ups of the disease over a period of 12 months after initial presentation of the disease, while a low risk of IBD progression may refer to a low risk that the individual will experience relapses or flares of the disease after initial presentation, in particular a low risk that the individual will experience on average 0.6 or more relapses or flare-ups of the disease over a period of 12 months after initial presentation of the disease.

The diagnosis of a relapse or flare-up of the disease is well within the capabilities of the skilled practitioner. For example, a relapse or flare-up of IBD in an individual may be characterised by a Harvey Bradshaw (disease activity) index>5; and (i) a C Reactive Protein (CRP) level of >10 mg/l, (ii) a calprotectin level of >200 µg/g, or (iii) endoscopic evidence of disease activity; and the individual having achieved remission following a previous flare-up of the disease. CRP is a blood marker of inflammation produced by the liver. Levels rise during an inflammatory event. CRP levels are usually measured in a blood sample obtained from the individual, while calprotectin levels are usually measured in a stool sample.

The Harvey Bradshaw (disease activity) index usually measures the following parameters:
  (i) general well-being (0=very well, 1=slightly below average, 2=poor, 3=very poor, 4=terrible)
  (ii) abdominal pain (0=none, 1=mild, 2=moderate, 3=severe)
  (iii) number of liquid stools per day
  (iv) abdominal mass (0=none, 1=dubious, 2=definite, 3=tender)
  (v) presence of complications (with one point for each complication present): arthralgia, uveitis, erythema nodosum, aphthous ulcers, Pyoderma gangrenosum, anal fissure, new fistula, abscess A Harvey Bradshaw index score >5 indicates the presence of mild to severe disease.

Known treatments for IBD include anti-inflammatory therapy, immunosuppressive therapy, and surgery. Examples of anti-inflammatory therapy include treatment with steroids (such as corticosteroids, e.g. prednisolone, or budesonide), and/or mesalazine. Examples of immunosuppressive therapy include treatment with TNFα inhibitors (such as infliximab), azathioprine, methotrexate, and/or 6-mercaptopurine.

Treatment may refer to treatment of ongoing disease intended to manage the disease (also referred to as maintenance therapy), as well as treatment of relapses or flare-ups of the disease.

A standard "step-up" treatment involves escalating therapy only in response to ongoing disease flare-ups or a failure of the disease to respond to initial treatment. For example, the initial flare-up of disease (at which a diagnosis is made) would be treated with an anti-inflammatory steroid, such as prednisolone, or an anti-inflammatory drug, such as mesalazine (e.g. in UC), but no maintenance therapy would be commenced. If a subsequent flare-up occurs, this treatment would be repeated and a maintenance therapy would then also be added (e.g. treatment with azathioprine, methotrexate, or 6-mercaptopurine). If flare-ups of the disease continued despite this maintenance therapy, a stronger maintenance therapy, such as treatment with a TNFα inhibitor (infliximab or adalimumab) would then be added. This treatment strategy prevents overtreatment—by only escalating therapy in response to inadequately controlled disease—but risks exposing patients with more progressive disease to substantial disease-related complications as treatments that are ultimately not effective at controlling the disease are trialled.

As already explained above, it has been found that early introduction of aggressive therapies in IBD, leads to better outcomes, compared to the standard step-up approach. Specifically, most patients who have active Crohn's disease are treated initially with corticosteroids. Although this approach usually controls symptoms, many patients become resistant to or dependent on corticosteroids, and prolonged exposure to corticosteroids is associated with an increased risk of mortality. A comparison of early use of combined immunosuppressive therapy using infliximab and azathioprine with conventional disease management showed that combined immunosuppressive therapy was more effective than conventional disease management for inducing remission and reducing corticosteroid use in patients who had been recently diagnosed with Crohn's disease. Initiation of more intensive treatment early in the course of the disease could therefore result in better outcomes for patients with IBD (D'Haens et al., 2008; Colombel et al., 2010). In particular, Crohn's disease patients treated with early combination immunosuppressive therapy (D'Haens et al., 2008) experience longer periods of steroid-free remission, are more likely to achieve mucosal healing and, ultimately, to avoid surgical resection (D'Haens et al., 2008; Colombel et al., 2010). However, this strategy is not suitable for all Crohn's disease patients as a proportion of patients would have achieved prolonged remission even with conventional corticosteroid treatment (Jess et al., 2007), and thus their treatment with combination immunosuppressive therapy would expose them to unnecessary side effects and toxicity.

The whole blood gene classifier identified by the present inventors predicts disease course in IBD, including Crohn's disease and ulcerative colitis. Specifically, patients in the IBD1 subgroup have a substantially higher incidence of relapses or flare-ups of the disease, resulting not only in a need for earlier treatment escalation but also more treatment escalations per unit time of follow up (compared to patients in the IBD2 group). This pattern of relapses or flare-ups of the disease is associated with considerable morbidity, and patients in the IBD1 subgroup are therefore most likely to benefit from early aggressive therapy, such as use of TNFα inhibitors.

Patients identified as being at high risk of IBD progression may therefore be treated with more aggressive therapy than normally administered early in the disease course, such as a "top-down" approach where patients are treated with a TNFα inhibitor, such as infliximab, in combination with azathioprine, methotrexate or 6-mercaptopurine at diagnosis, with subsequent relapses or flare-ups being treated with additional administration of an anti-inflammatory steroid, such as prednisolone, an increased administration of the TNFα inhibitor, or treatment with an anti-integrin antibody, for example.

In the case of an individual identified as one who is at high risk of IBD progression, treatment may thus comprise treating, or selecting the individual for treatment, with a more frequent or more aggressive disease treatment regimen, or with a disease regimen not normally administered during the maintenance phase of IBD. A more frequent or more aggressive disease treatment regimen may refer to a disease treatment regimen that is more frequent or more intense than the treatment normally administered during the maintenance phase of IBD. An example of a more aggressive disease treatment regimen is treatment with one or more immunosuppressants, such as treatment with a TNFα inhibitor, such as infliximab, in combination with azathioprine, 6-mercaptopurine, or methotrexate, e.g. at diagnosis.

In the case of an individual identified as one who is at low risk of IBD progression, treatment may comprise treating, or selecting the individual for treatment, with the standard step-up treatment approach described above. The standard step-up approach avoids unnecessary overtreatment of such patients. Thus, an individual identified as one who is at low risk of IBD progression, may be treated, or selected for treatment, with an inflammatory steroid, such as prednisolone, or an anti-inflammatory drug, such as mesalazine, at initial presentation of the disease. A subsequent relapse, or flare-up, of the disease may be treated with an inflammatory steroid, such as prednisolone, or an anti-inflammatory drug, such as mesalazine, in combination with administration of a maintenance therapy, such as treatment with azathioprine, methotrexate, or 6-mercaptopurine. Further relapses, or flare-ups, of the disease may be treated with an inflammatory steroid, such as prednisolone, or an anti-inflammatory drug, such as mesalazine, in combination with administration of a TNFα inhibitor (such as infliximab or adalimumab) as maintenance therapy.

The methods of the present invention involve the use of whole blood samples obtained from one or more individuals and thus are in vitro methods.

The present invention provides an in vitro method comprising determining the expression level of two or more genes selected from the group consisting of: ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3, in a whole blood sample obtained from an individual.

The methods of the present invention are expected to find application in methods to identify a substance capable of treating IBD in an individual, such as clinical trials. The individual employed in such a method may be at high risk or low risk of IBD progression, preferably the individual is at high risk of IBD progression. An individual who is at high risk of IBD progression is expected to experience more frequent relapses or flare-ups of the disease than an individual who is at low risk of IBD progression, thus making it easier to evaluate the efficacy of the putative treatment, e.g. in reducing the frequency and/or severity of such flare-ups or relapses.

A method, preferably an in vitro method, of identifying a substance capable of treating IBD in an individual may comprise:
(i) identifying an individual who is at high risk or low risk of IBD progression, preferably at high risk of IBD progression, using a method of the invention; and
(ii) comparing the level of IBD progression in the individual, wherein the individual has been subjected to treatment with the substance of interest, with a control. A lower level of IBD progression in the individual compared with the control indicates that the substance is capable of treating IBD. A lower level of IBD progression may refer to a reduction in the frequency and/or severity of flare-ups or relapses of IBD compared with the control. The method may further comprise a step of subjecting the individual to treatment with the substance of interest following step (i) and prior to step (ii) in the above method. The control may be the level of IBD progression observed in an individual, or group of individuals, identified to be at high risk or low risk, preferably at high risk, of IBD progression using e.g. a method of the present invention, which have not been treated with the substance of interest.

A method of identifying a substance capable of treating IBD in an individual may thus comprise:
(i) identifying a first individual who is at high risk or low risk of IBD progression, preferably at high risk of IBD progression, using a method of the invention;
(ii) identifying a second individual who is at high risk or low risk of IBD progression, preferably at high risk of IBD progression, using a method of the invention; and
(iii) comparing the level of IBD progression in the first individual with the level of IBD progression in the second individual, wherein the first individual has been subjected to treatment with the substance of interest, and wherein a lower level of IBD progression in the first individual compared with the second individual indicates that the substance is capable of treating IBD. The method may optionally further comprise a step of treating the first individual with the substance of interest following step (i) but prior to step (iii).

The methods of the present invention are also expected to find application in methods to identify a substance capable of inducing a low risk (IBD2) phenotype in an IBD patient. The patient employed in such a method is at high risk of IBD progression. Specifically, the present invention provides a method, preferably an in vitro method, of identifying a substance capable of inducing a low risk (IBD2) phenotype in an IBD patient, the method comprising:
providing (i) a whole blood sample obtained from an IBD patient prior to treatment with a substance of interest, and (ii) a whole blood sample obtained from the IBD patient following treatment with the substance of interest, wherein the IBD patient has been determined to have a high risk (IBD1) phenotype using a method according to the present invention; and
determining the expression level of two or more genes selected from the group consisting of ARRDC4, GBP5, P2RY14, VTRNA1-1, IL18RAP, HP, NUDT7, GZMH, TRGC2, GZMK, LGALSL, FCRL5, IF144L, LINC01136, LY96, and TRGV3 in samples (i) and (ii);
wherein a lower expression of genes ARRDC4, GBP5, P2RY14, VTRNA1-1, IL18RAP, HP, NUDT7, GZMH, TRGC2, and GZMK, and a higher expression of genes LGALSL, FCRL5, IF144L, LINC01136, LY96, and TRGV3 in sample (ii) relative to sample (i) indicates that the substance is capable of inducing a low risk (IBD2) phenotype in an IBD patient.

A substance identified as capable of treating IBD or inducing a low risk (IBD2) phenotype in an IBD patient may further be formulated into a medicament. In addition to the substance, such a medicament may comprise, for example, a pharmaceutically acceptable excipient.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXAMPLES

Example 1

Identification of an IBD1/IBD2 Gene Signature in Whole Blood

Materials and Methods

Patient Recruitment for Gene Expression Profiling

Sixty-nine patients with active Crohn's disease (CD) (n=39) and ulcerative colitis (UC) (n=30) were recruited prior to commencing treatment and follow-up data subsequently collected as already described in (Lee et al., 2011). Ethical approval for this work was obtained from the Cambridgeshire Regional Ethics Committee (REC08/H0306/21). All participants provided written informed consent.

CD8+ T Cells Samples

CD8+ T cells were positively selected from blood samples obtained from the sixty-nine patients according to the methods described in (Lyons et al., 2007) and RNA was extracted using RNEasy Mini Kits (Qiagen) according to the manufacturer's instructions, as previously described in (Lee et al., 2011).

Whole Blood Samples 2.5 ml of whole blood was collected from the sixty-nine patients into RNeasy mini or PAXgene Blood RNA Tube IVD (Qiagen) in order to immediately fix the RNA (Rainen et al., 2002). Collected samples were stored according to the manufacturer's instructions and RNA was subsequently extracted using the PAXgene Blood RNA Kit IVD (Qiagen).

RNA Quantification

RNA quantity and quality were determined using a Nanodrop 1000 spectrophotometer (Thermo Scientific) and an Agilent 2100 Bioanalyser (Agilent Technologies) respectively.

Whole Blood Gene Expression Profiling 200ng total RNA was processed and hybridized onto Affymetrix Human Gene ST 1.0 microarrays (CD8+ RNA samples) or Affymetrix Human Gene ST 2.0 (whole blood RNA samples) which were then washed and scanned according to the manufacturer's instructions.

Microarray Data Processing

Microarray raw data were processed in R using the preprocessCore package (Bolstad, 2013) in BioConductor (Huber et al., 2015). Briefly, raw data were background corrected, quantile-normalised and summarised using the code reported in listing 4.1. Presence of potential outliers was assessed using the package arrayQualityMetrics (Kauffmann et al., 2009). Batch correction was performed using ComBat (Johnson et al., 2007). Importantly, knowledge about IBD1/IBD2 membership of individual samples was not incorporated in the batch correction procedure, in order to avoid any downward bias in the generalisation error estimate by leave-one-out cross-validation. Only probe sets detecting expressed transcripts (defined as probe sets showing a log 2 expression signal >7.0 in at least 75% of samples) were retained. Unexpressed probe sets and probe sets without annotation were removed from the dataset, leaving 12,874 probe sets for the whole-blood gene expression dataset.

Quantitative PCR

Levels of mRNA for candidate genes and three reference genes were determined using TaqMan Expression Assays (Life Technologies) on a Roche LightCycler 480 real time PCR instrument according to the manufacturer's instructions. PCR conditions were optimised to minimise intra- and inter-plate variation. Transcript abundance was calculated using the $\Delta\Delta$CT method (Livak et al., 2001). A cDNA sample derived from pooled RNA extracted from whole-blood of healthy individuals was included in each plate and used as a calibrator. Each measurement was repeated three times and the median of the three technical replicates was used in the final analysis.

IBD1/IBD2 Patient Classification Based on CD8+ T Cell Gene Expression Data

To assign IBD1 (poor prognosis) or IBD2 (good prognosis) status to the sixty-nine patients, normalised expression data from the patients' CD8+ T cell samples was merged with data from the inventor's existing IBD patient cohort. Consensus clustering of the merged dataset was then used to stratify the cohort into the two previously identified prognostic groups, as described in Lee et al., 2011.

Patients in the IBD1 subgroup have a substantially higher incidence of relapses or flare-ups of the disease, characterised not only by an earlier need for treatment escalation but also by a requirement for more treatment escalations per unit time of follow up (compared to patient in the IBD2 group).

IBD1/IBD2 Patient Classification Based on Whole Blood Gene Expression Data

In parallel, a dataset of whole blood gene expression data from the sixty-nine IBD patients was also generated. A number of genes necessary to stratify patients into the two prognostic groups (IBD1 and IBD2) based on the whole blood gene expression data were selected by applying a logistic regression model with adaptive elastic net regularization to the whole blood gene expression dataset. The selected candidate genes and several closely correlated genes were taken forward for testing using real time PCR analysis.

Figure 2:
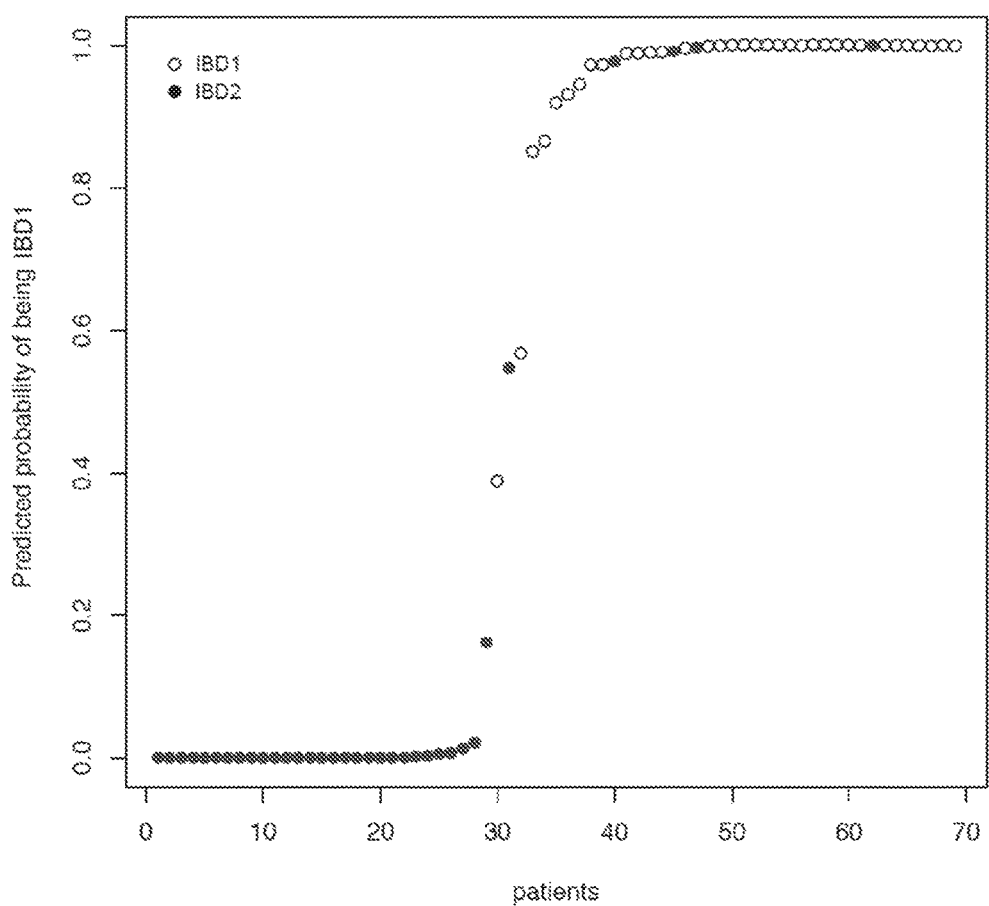
FIG. 2 shows a plot demonstrating the predicted probability of each patient belonging to the IBD1 group, according to the qPCR classifier (Table 1). Empty dots: IBD1 patients; filled dots: IBD2 patients.

Taqman real time PCR assays were performed for each candidate gene together with 10 invariant reference genes. An elastic net regularised regression model was applied to the real time PCR data to identify an optimal model, comprised of 15 genes, that was able to stratify the cohort of 69 IBD patients into the two original prognostic groups, IBD1 and IBD2 (PPV=0.87, NPV=0.94, sensitivity 0.94, specificity 0.85; FIGS. 1 and 2). The IBD1 and IBD2 subgroups also demonstrated an equivalent association with disease course, both in terms of escalation-free survival (P=0.0074) and number of escalations over time (P=0.0003, mean number of treatment escalations: 1.62 (IBD1), 0.70 (IBD2). The 15 genes are listed in Table 1.

TABLE 1

| No. | Gene symbol | Gene name |
|---|---|---|
| 1 | ARRDC4 | Arrestin domain containing 4 |
| 2 | GBP5 | Guanylate binding protein 5 |
| 3 | P2RY14 | Purinergic receptor P2Y, G-protein coupled, 14 |
| 4 | VTRNA1-1 | Vault RNA 1-1 |

TABLE 1-continued

| No. | Gene symbol | Gene name |
|---|---|---|
| 5 | IL18RAP | Interleukin 18 receptor accessory protein |
| 6 | HP | Haptoglobin |
| 7 | NUDT7 | Nudix (nucleoside diphosphate linked moiety X)-type motif 7 |
| 8 | GZMH | Granzyme H |
| 9 | TRGC2/TARP/TRGJI | T cell receptor gamma constant 2/T cell receptor gamma joining 1 |
| 10 | ZNF493 | Zinc finger protein 493 |
| 11 | LGALSL | Lectin, galactoside-binding-like |
| 12 | FCRL5 | Fc receptor-like 5 |
| 13 | IFI44L | Interferon-induced protein 44-like |
| 14 | LINC01136 | Long intergenic non-protein coding RNA 1136 |
| 15 | LY96 | Lymphocyte antigen 96 |

Example 2

Optimisation of the Whole Blood Classifier for RT-qPCR Analysis

The genes identified in Example 1 were taken forward to real time qPCR assay development, where the final content of the whole blood classifier (16 informative and 2 reference genes) was optimised and finalised. The informative genes forming part of this classifier are listed in Table 2 below.

Through being detectable in whole blood by methods such as RT-qPCR, stratification of patients using this whole blood gene classifier will be simpler and more cost effective than tests requiring the isolation of particular cell types prior to determining gene expression, as described in WO2010/084312, for example.

Furthermore, the whole blood gene classifier is expected to have wide-ranging healthcare benefits, including leading directly to major improvements in IBD management; enabling patients with aggressive disease to receive appropriately potent therapy from diagnosis, while ensuring that those with indolent disease are not exposed to the risks and side-effects of unnecessary immunosuppression. This is expected to improve clinical outcomes, by minimising treatment toxicity and reducing disease complications and healthcare costs. The whole blood gene classifier is also expected to facilitate the pre-selection of patients for clinical trials based upon likelihood of disease flare, thereby reducing the number of patients required for trials of flare prevention or treatment by a factor of 2 to 3.

TABLE 2

| No. | Gene symbol | Gene name | Upregulated/downregulated in subtype IBD1 | Gene ID | NCBI accession number | NCBI GI number |
|---|---|---|---|---|---|---|
| 1 | ARRDC4 | Arrestin domain containing 4 | upregulated | 91947 | NM_183376.2 | 190886441 |
| 2 | GBP5 | Guanylate binding protein 5 | upregulated | 115362 | NM_052942.3 | 197333735 |
| 3 | P2RY14 | Purinergic receptor P2Y, G-protein coupled, 14 | upregulated | 9934 | NM_001081455.1 | 125625353 |
| 4 | VTRNA1-1 | Vault RNA 1-1 | upregulated | 56664 | NR_026703.1 | 222352136 |
| 5 | IL18RAP | Interleukin 18 receptor accessory protein | upregulated | 8807 | NM_003853.3 | 588480507 |
| 6 | HP | Haptoglobin | upregulated | 3240 | NM_005143.4 | 970259872 |
| 7 | NUDT7 | Nudix (nucleoside diphosphate linked moiety X)-type motif 7 | upregulated | 283927 | NM_001105663.2 | 343887368 |
| 8 | GZMH | Granzyme H | upregulated | 2999 | NM_033423.4 | 399124766 |
| 9 | TRGC2/TARP/TRGJI | T cell receptor gamma constant 2/T cell receptor gamma joining 1 | upregulated | 6967 | BC039116.1 | 25058606 |
| 10 | GZMK | Granzyme K | upregulated | 3003 | NM_002104.2 | 73747815 |
| 11 | LGALSL | Lectin, galactoside-binding-like | downregulated | 29094 | NM_014181.2 | 156151365 |
| 12 | FCRL5 | Fc receptor-like 5 | downregulated | 83416 | NM_031281.2 | 157694525 |
| 13 | IFI44L | Interferon-induced protein 44-like | downregulated | 10964 | NM_006820.3 | 732662992 |
| 14 | LINC01136 | Long intergenic non-protein coding RNA 1136 | downregulated | 730227 | NR_034151.1 | 300796286 |
| 15 | LY96 | Lymphocyte antigen 96 | downregulated | 23643 | NM_015364.4 | 307775406 |
| 16 | TRGV3 | T Cell Receptor Gamma Variable 3 | downregulated | 6976 | BC071739.1 | 47938244 |

Example 3

Independent Validation of the qPCR-Based Whole Blood Assay

Independent validation of the prognostic performance of the 16 gene classifier identified in Example 2 was then performed using a second, independent, cohort of 85 newly diagnosed IBD patients from 4 sites around the UK (Cambridge, Nottingham, Exeter, and London). Analysis of whole blood gene expression using the qPCR-based test developed in Example 2 replicated the prognostic stratification seen in the discovery cohort with a IBD1/IBD2 Hazard ratio of 3.52 (95 percent confidence interval [CI]: 1.84-6.76, P=0.0002, FIG. 3). This performance compares favourably to that of existing gene expression based in vitro diagnostic tests. For example, the Hazard ratio for Oncotype DX, a gene expression diagnostic that predicts breast cancer recurrence, is 2.81 (95% CI: 1.70 4.64) (Paik et al., NEJM, 2004).

Example 4

Minimal Gene Classifier

To determine the minimum number of genes of the optimised whole blood classifier developed in Example 2 necessary to stratify patients into the two prognostic groups, IBD1 and IBD2, the inventors performed an exhaustive computational analysis of all possible combinations of the 16 genes identified in Example 2 to determine the minimum number of genes which could be used to accurately stratify IBD patients into the IBD1 and IBD2 subgroups.

For each possible combination of n genes (with 1<=n<=16), an L2 regularised logistic regression model was fitted to the relevant qPCR gene expression data and the associated predictive performance for each model was evaluated as already described in Example 1.

The results listed in Table 3 below show that whole blood gene expression data from as few as two genes selected from the optimised 16-gene whole blood classifier identified in Example 2 could be used to accurately stratify IBD patients into the IBD1 and IBD2 subgroups. Specifically, measuring expression of genes IL18RAP and TRGC2 in whole blood samples obtained from IBD patients was sufficient to stratify patients into the IBD1 and IBD2 subgroups with an accuracy of 0.71 (sensitivity: 0.73; specificity: 0.69; PPV: 0.69; NPV: 0.74).

Similarly, whole blood gene expression data for three genes selected from the optimised whole blood classifier developed in Example 2 was shown to be suitable for accurately stratify IBD patients into the IBD1 and IBD2 subgroups. For example, measuring expression of genes IL18RAP, TRGC2 and TRGV3 in whole blood samples obtained from IBD patients was sufficient to stratify patients into the IBD1 and IBD2 subgroups with an accuracy of 0.74 (sensitivity: 0.74; specificity: 0.74; PPV: 0.74; NPV: 0.74).

Combinations of 4, 5, 6, 7, 8, 9, 10, 11, 12, 13, 14 and 15 genes from the genes listed in Table 2 were similarly tested and found to be suitable for stratifying IBD patients into the IBD1 and IBD2 subgroups with an accuracy of 0.7 or above, as shown in Table 3.

It must be noted that for each number of genes tested, Table 3 only reports the combination of genes which resulted in optimal stratification of the IBD patients into the IBD1 and IBD2 subgroups. For example, only the combination of four genes allowing optimal stratification of the IBD patients into the IBD1 and IBD2 subgroups is shown in Table 3. However, other combinations of four genes selected from the 16-gene classifier identified in Example 2 were also suitable for stratifying IBD patients into the IBD1 and IBD2 subgroups with an accuracy of 0.7 or above.

Measuring expression of all 16 genes in whole blood samples obtained from IBD patients stratified patients into the IBD1 and IBD2 subgroups with an accuracy of 0.971 (PPV=1.000; NPV=0.941; sensitivity: 0.946; and specificity: 1.000)

TABLE 3

| No. of genes in classifier | Accuracy | Sensitivity | Specificity | Pos Pred. Value | Neg Pred. Value | Hazard Ratio | logrank.p | Genes included in optimal classifier |
|---|---|---|---|---|---|---|---|---|
| 1 | 0.623 | 0.655 | 0.600 | 0.543 | 0.706 | 1.439 | 0.265663969 | TRGV3 |
| 2 | 0.710 | 0.727 | 0.694 | 0.686 | 0.735 | 2.012 | 0.033898248 | IL18RAP, TRGC2 |
| 3 | 0.739 | 0.743 | 0.735 | 0.743 | 0.735 | 1.776 | 0.082653382 | IL18RAP, TRGC2,TRGV3 |
| 4 | 0.783 | 0.778 | 0.788 | 0.800 | 0.765 | 2.274 | 0.014241606 | IL18RAP, LOC730227, TRGC2, VTRNA1_1 |
| 5 | 0.812 | 0.806 | 0.818 | 0.829 | 0.794 | 2.314 | 0.013031682 | IL18RAP, LOC730227, TRGC2, TRGV3, VTRNA1_1 |
| 6 | 0.826 | 0.848 | 0.806 | 0.800 | 0.853 | 1.950 | 0.042996294 | IL18RAP, LGALSL, LOC730227, TRGC2, TRGV3, VTRNA1_1 |
| 7 | 0.855 | 0.838 | 0.875 | 0.886 | 0.824 | 1.774 | 0.086038034 | FCRL5, LOC730227, NUDT7, P2RY14, TRGC2, TRGV3, VTRNA1_1 |
| 8 | 0.870 | 0.882 | 0.857 | 0.857 | 0.882 | 2.848 | 0.001823014 | FCRL5, GBP5, IFI44L, IL18RAP, LGALSL, TRGC2, TRGV3, VTRNA1_1 |
| 9 | 0.884 | 0.886 | 0.882 | 0.886 | 0.882 | 2.281 | 0.012903601 | ARRDC4, GBP5, HP, IL18RAP, LGALSL, LOC730227, LY96, P2RY14, VTRNA1_1 |
| 10 | 0.884 | 0.886 | 0.882 | 0.886 | 0.882 | 2.124 | 0.022933794 | FCRL5, GBP5, IFI44L, IL18RAP, LGALSL, LOC730227, P2RY14, TRGC2, TRGV3, VTRNA1_1 |
| 11 | 0.913 | 0.914 | 0.912 | 0.914 | 0.912 | 2.439 | 0.007083716 | ARRDC4, FCRL5, GBP5, HP, IFI44L, IL18RAP, LOC730227, LY96, |

TABLE 3-continued

| No. of genes in classifier | Accuracy | Sensitivity | Specificity | Pos Pred. Value | Neg Pred. Value | Hazard Ratio | logrank.p | Genes included in optimal classifier |
|---|---|---|---|---|---|---|---|---|
| 12 | 0.928 | 0.917 | 0.939 | 0.943 | 0.912 | 2.588 | 0.004515272 | ARRDC4, FCRL5, GBP5, HP, IFI44L, IL18RAP, LGALSL, LOC730227, LY96, P2RY14, TRGC2, VTRNA1_1 |
| 13 | 0.928 | 0.917 | 0.939 | 0.943 | 0.912 | 2.711 | 0.003123373 | ARRDC4, FCRL5, GBP5, GZMH, HP, IFI44L, IL18RAP, LGALSL, LOC730227, LY96, P2RY14, TRGV3, VTRNA1_1 |
| 14 | 0.913 | 0.892 | 0.938 | 0.943 | 0.882 | 2.023 | 0.034300476 | FCRL5, GBP5, GZMK, HP, IFI44L, IL18RAP, LGALSL, LOC730227, LY96, NUD17, P2RY14, TRGC2, TRGV3, VTRNA1_1 |
| 15 | 0.942 | 0.897 | 1.000 | 1.000 | 0.882 | 2.573 | 0.005854707 | ARRDC4, FCRL5, GBP5, GZMH, GZMK, HP, IFI44L, IL18RAP, LGALSL, LOC730227, LY96, NUDT7, P2RY14, TRGV3 VTRNA1_1 |
| 16 | 0.971 | 0.946 | 1.000 | 1.000 | 0.941 | 2.616 | 0.004390451 | ARRDC4, FCRL5, GBP5, GZMH, GZMK, HP, IFI44L, IL18RAP, LGALSL, LOC730227, LY96, NUDT7, P2RY14, TRGC2, TRGV3, VTRNA1_1 |

Comparative Example 5

Figure 4:
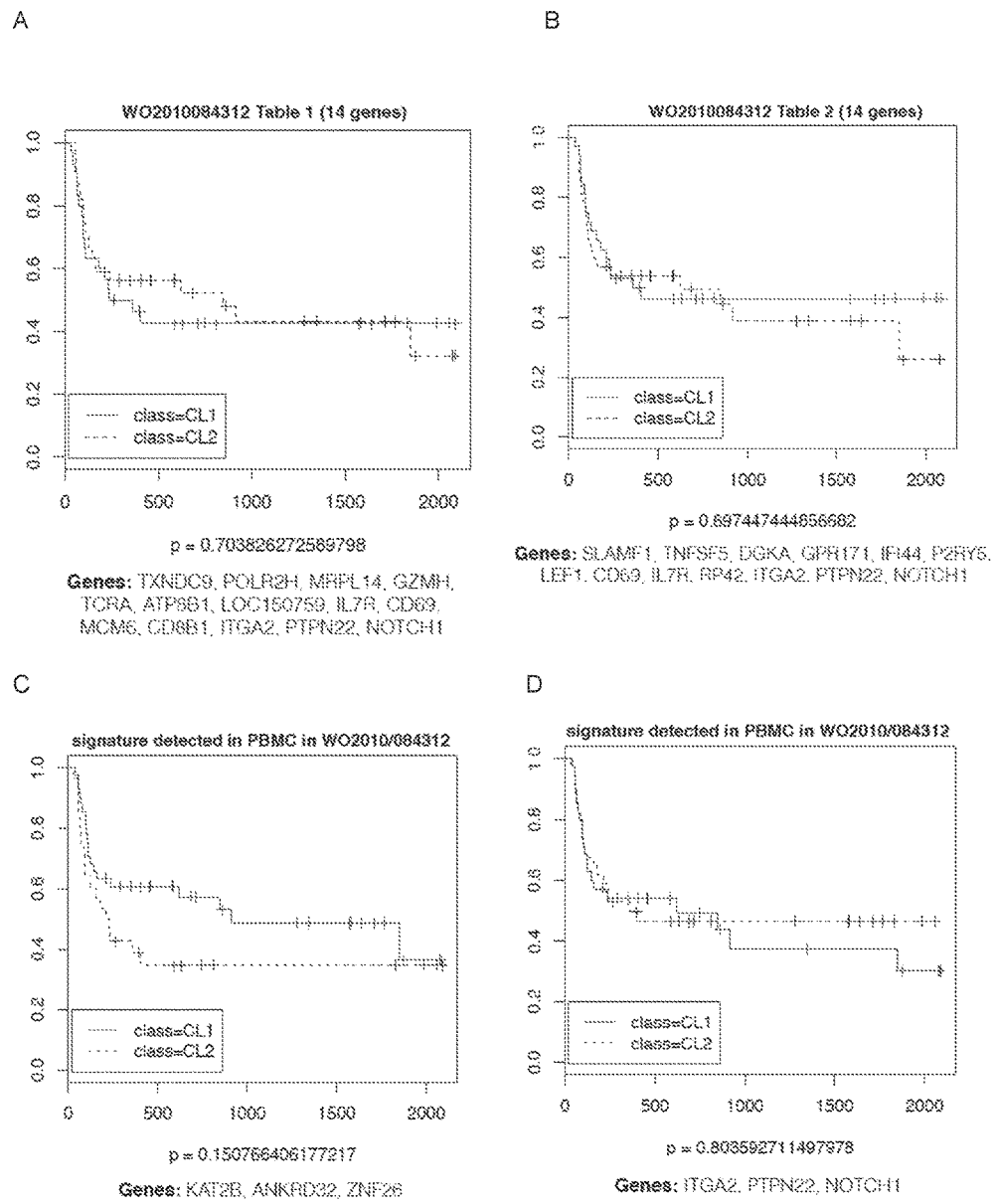
FIG. 4 shows Kaplan-Meier plots comparing treatment escalation-free survival between the IBD1/IBD2 groups predicted using the gene expression signatures described in WO2010/084312. p: Log-rank test p-value. CL1 and CL2 refer to the IBD1 and IBD2 subgroups, respectively.

The present inventors tested the ability of the gene expression signatures previously described in WO2010/084312 to correctly stratify patients into the high risk IBD1 and low risk IBD2 subgroups based on whole blood gene expression data, as already described in Example 1. Measuring expression of the genes disclosed in Tables 1 or 2 of WO2010/084312, or genes KAT2B, ANKRD32 and ZNF26, or ITGA2, PTPN22 and NOTCH1, described in WO2010/084312, in whole blood did not result in an accurate classification of the IBD patients into the IBD1 and IBD2 subgroups, as indicated by the Log-rank test p-values reported below the relevant graphs (see FIG. 4). These results demonstrate that the gene signatures disclosed in WO2010/084312 are not suitable for assessing whether an individual is at high risk or low risk of IBD progression when gene expression is measured in whole blood.

Example 6

Patient Classification Using a 3-, 4-, 5-, 13-, 14-, and 16-Gene Model

The method of the invention stratifies patients into patient's having a high or low risk of IBD progression, requiring collection of only 2.5 ml of whole blood in a collection tube that facilitates stability of RNA material and may be posted internationally (as the RNA remains stable at room temperature for up to 3 days). The assay returns a rapid result within 48 hours and measures gene expression via quantitative RT-PCR for a patient diagnosis, prior to starting treatment.

The result of each RT-PCR measurement relies upon an algorithm to apply specific weighting to return an outcome prediction (high/low risk of IBD progression) with a validated odds ratio of 3.5 between high and low risk outcome groups.

Patient Classification Using a 3-, 4-, 5-, 13-, 14-, and 16-gene Model

To determine their likely disease course patients 429 and 483 provided blood samples in PAXGene® Blood RNA tubes. Following RNA extraction and cDNA synthesis, the expression levels of 16 informative genes (ARRDC4, FCRL5, GBP5, GZMH, GZMK, HP, IFI44L, IL18RAP, LGALSL, LINC01136, LY96, NUDT7, P2RY14, TRGC2, TRGV3 and VTRNA1-1) and 2 reference genes (RNA18S5 and CDV3) were determined by quantitative PCR using a Roche Lightcycler 480 (Ct, Table 4). The raw data was normalised by subtracting the mean value of the 2 reference genes from each informative gene (dCt, Table 4), and then standardised by mean centring (dCt', Table 4).

TABLE 4

Raw and normalised expression data for individual test assays

| Assay | Patient 429 | | | Patient 483 | | |
|---|---|---|---|---|---|---|
|  | Ct | dCt | dCt' | Ct | dCt | dCt' |
| ARRDC4 | 35.84 | 14.64 | 0.52 | 35.11 | 15.00 | −1.48 |
| FCRL5 | 35.01 | 13.81 | −0.34 | 35.24 | 15.13 | 0.81 |
| GBP5 | 29.07 | 7.87 | −0.53 | 26.32 | 6.20 | −1.70 |
| GZMH | 31.46 | 10.26 | −0.21 | 27.77 | 7.66 | −2.61 |
| GZMK | 33.44 | 12.24 | −0.86 | 31.86 | 11.74 | −0.88 |
| HP | 32.31 | 11.11 | −0.10 | 30.72 | 10.61 | −0.72 |
| IFI44L | 34.85 | 13.65 | −0.43 | 33.03 | 12.92 | −0.55 |
| IL18RAP | 31.14 | 9.94 | −1.43 | 31.22 | 11.11 | −0.67 |
| LGALSL | 32.28 | 11.08 | 0.32 | 30.56 | 10.44 | −1.31 |
| LINC01136 | 35.40 | 14.20 | −0.46 | 34.97 | 14.85 | 0.11 |
| LY96 | 35.40 | 14.20 | −0.32 | 34.22 | 14.11 | −1.18 |
| NUDT7 | 37.35 | 16.15 | 0.32 | 36.54 | 16.43 | 0.62 |
| P2RY14 | 37.56 | 16.36 | −0.91 | 34.90 | 14.79 | −1.63 |

TABLE 4-continued

Raw and normalised expression data for individual test assays

| Assay | Patient 429 | | | Patient 483 | | |
|---|---|---|---|---|---|---|
| | Ct | dCt | dCt' | Ct | dCt | dCt' |
| TRGC2 | 38.25 | 17.05 | 2.34 | 32.99 | 12.88 | −1.06 |
| TRGV3 | 40.86 | 19.66 | −0.32 | 37.41 | 17.30 | −0.65 |
| VTRNA1-1 | 33.45 | 12.25 | 1.26 | 31.81 | 11.70 | 0.56 |
| CDV3 (Reference) | 30.10 | — | — | 28.79 | — | — |
| RNA18S5 (Reference) | 12.30 | — | — | 11.44 | — | — |

The risk score, expressed as probability (P), of either patient experiencing mild disease (low risk of IBD progression) can be determined by applying the following logistic regression model to the standardised gene expression data using a 3-gene model (equation (1)), a 4-gene model (equation (2)), a 5-gene model (equation (3)), 13-gene model (equation (4)), a 14-gene model (equation (5)), and a 16-gene model (equation (6)).

$$Logit(P_{severe}) = \beta_0 + \beta_1(IL18RAP) + \beta_2(TRGC2) + \beta_3(TRGV3) \quad (1)$$

$$Logit(P_{severe}) = \beta_0 + \beta_1(IL18RAP) + \beta_2(LINC01136) + \beta_3(TRGC2) + \beta_4(VTRNA1\text{-}1) \quad (2)$$

$$Logit(P_{severe}) = \beta_0 + \beta_1(IL18RAP) + \beta_2(LINC01136) + \beta_3(TRGC2) + \beta_4(TRGV3) + \beta_5(VTRNA1\text{-}1) \quad (3)$$

$$Logit(P_{severe}) = \beta_0 + \beta_1(ARRDC4) + \beta_2(FCRL5) + \beta_3(GBP5) + \beta_4(GZMH) + \beta_5(HP) + \beta_6(IFI44L) + \beta_7(IL18RAP) + \beta_8(LGALSL) + \beta_9(LINC01136) + \beta_{10}(LY96) + \beta_{11}(P2RY14) + \beta_{12}(TRGV3) + \beta_{13}(VTRNA1\text{-}1) \quad (4)$$

$$Logit(P_{severe}) = \beta_0 + {}_1(FCRL5) + \beta_3(GBP5) + \beta_4(GZMK) + \beta_5(HP) + \beta_6(IFI44L) + \beta_7(IL18RAP) + \beta_8(LGALSL) + \beta_9(LINC01136) + \beta_{10}(LY96) + \beta_{11}(NUDT7) + \beta_{12}(P2RY14) + \beta_{13}(TRGC2) + \beta_{14}(TRGV3) \quad (5)$$

$$Logit(P_{severe}) = \beta_0 + \beta_1(ARRDC4) + \beta_2(FCRL5) + \beta_3(GBP5) + \beta_4(GZMH) + \beta_5(GZMK) + \beta_6(HP) + \beta_7(IFI44L) + \beta_8(IL18RAP) + \beta_9(LGALSL) + \beta_{10}(LINC01136) + \beta_{11}(LY96) + \beta_{12}(NUDT7) + \beta_{13}(P2RY14) + \beta_{14}(TRGC2) + \beta_{15}(TRGV3) + \beta_{16}(VTRNA1\text{-}1) \quad (6)$$

Individual weightings ranging from −60 to 60, −30 to 30, or −10 to 10 are then applied to the standardized gene expression data for each gene in the model. Individual weightings (beta) for each assay are as shown in Table 5.

TABLE 5

Gene weightings for 3-, 4-, 5-, 13-, 14-, and 16-gene models

| | Beta values | | | | | |
|---|---|---|---|---|---|---|
| | 3 gene model | 4 gene model | 5 gene model | 13 gene model | 14 gene model | 16 gene model |
| Model intercept term ($\beta_0$) | 0.07 | 0 | 0.03 | −0.74 | 0.04 | 0.81 |
| ARRDC4 | — | — | — | −2.39 | — | −3.13 |
| FCRL5 | — | — | — | 2.78 | 1.22 | 5.56 |
| GBP5 | — | — | — | −7.12 | −2.88 | −9.38 |
| GZMH | — | — | — | −2.84 | — | −2.86 |
| GZMK | — | — | — | — | −1.28 | −3.25 |
| HP | — | — | — | −3.18 | −1.32 | −5.12 |
| IFI44L | — | — | — | 5.86 | 1.51 | 5.22 |
| IL18RAP | −0.75 | −1 | −0.27 | −3.47 | −1.6 | −5.19 |

TABLE 5-continued

Gene weightings for 3-, 4-, 5-, 13-, 14-, and 16-gene models

| | Beta values | | | | | |
|---|---|---|---|---|---|---|
| | 3 gene model | 4 gene model | 5 gene model | 13 gene model | 14 gene model | 16 gene model |
| LGALSL | — | — | — | 1.97 | 1.54 | 4.17 |
| LINC01136 | — | 0.9 | 0.24 | 4.33 | −1.14 | 5.97 |
| LY96 | — | — | — | 4.51 | 1.43 | 5.98 |
| NUDT7 | — | — | — | — | −1.14 | −3.91 |
| P2RY14 | — | — | — | −4.08 | −1.03 | −2.73 |
| TRGC2 | −0.85 | −0.8 | −0.25 | — | −1.35 | −1.85 |
| TRGV3 | 1 | — | 0.25 | 1.47 | 1.71 | 3.89 |
| VTRNA1-1 | — | −0.8 | −0.22 | −5.96 | −2.25 | −6.83 |

3-gene Model

Rearranging equation (1) the probability of patient 429 following a severe disease course is given by:

$$P_{severe} = \frac{\exp^{0.07+(-0.75^*-1.42)+(-0.85^*2.34)+(1^*-0.31)}}{1+\exp^{0.07+(-0.75^*-1.42)+(-0.85^*2.34)+(1^*-0.31)}}$$

$$P_{severe} = 0.24$$

Since $P_{severe} < 0.5$ patient 429 is predicted to follow a mild disease course.

Similarly, for patient 483:

$$P_{severe} = \frac{\exp^{0.07+(-0.75^*-0.67)+(-0.85^*-1.05)+(1^*-0.65)}}{1+\exp^{0.07+(-0.75^*-0.67)+(-0.85^*-1.05)+(1^*-0.65)}}$$

$$P_{severe} = 0.45$$

Since $P_{severe} < 0.5$ patient 483 is predicted to follow a mild disease course.

4-gene Model

Rearranging equation (2) the probability of patient 429 following a severe disease course is given by:

$$P_{severe} = \frac{\exp^{0+(-1^*-1.42)+(0.9^*-0.45)+(-0.8^*2.34)+(-0.8^*1.26)}}{1+\exp^{0+(-1^*-1.42)+(0.9^*-0.45)+(-0.8^*2.34)+(-0.8^*1.26)}}$$

$$P_{severe} = 0.13$$

Since $P_{severe} < 0.5$ patient 429 is predicted to follow a mild disease course.

Similarly, for patient 483:

$$P_{severe} = \frac{\exp^{0+(-1^*-0.67)+(0.9^*-0.10)+(-0.8^*-1.0)+(-0.8^*0.55)}}{1+\exp^{0+(-1^*-0.67)+(0.9^*-0.10)+(-0.8^*-1.0)+(-0.8^*0.55)}}$$

$$P_{severe} = 0.73$$

Since $P_{severe} > 0.5$ patient 483 is predicted to follow a severe disease course.

5-gene Model

Rearranging equation (3) the probability of patient 429 following a severe disease course is given by:

$$P_{severe} = \frac{\exp^{0.03+(-0.27*-1.42)+(0.24*-0.45)+(-0.25*2.34)+(0.25*-0.31)+(-0.22*1.26)}}{1+\exp^{0.03+(-0.27*-1.42)+(0.24*-0.45)+(-0.25*2.34)+(0.25*-0.31)+(-0.22*1.26)}}$$

$$P_{severe} = 0.35$$

Since $P_{severe} < 0.5$ patient 429 is predicted to follow a mild disease course.

Similarly, for patient 483:

$$P_{severe} = \frac{\exp^{0.03+(-0.27*-0.67)+(0.24*0.1)+(-0.25*-1.05)+(0.25*-0.65)+(-0.22*0.55)}}{1+\exp^{0.03+(-0.27*-0.67)+(0.24*0.1)+(-0.25*-1.05)+(0.25*-0.65)+(-0.22*0.55)}}$$

$$P_{severe} = 0.55$$

Since $P_{severe} > 0.5$ patient 483 is predicted to follow a severe disease course (high risk of IBD progression).

13-gene Model

Rearranging equation (4) the probability of patient 429 following a severe disease course is given by:

$$P_{severe} = \frac{\exp^{\substack{-0.74+(-2.39*0.52)+(2.78*-0.33)+(-7.12*-0.53)+(-2.84*-0.21)+(-3.18*-0.10)+\\(5.86*-0.42)+(-3.47*-1.42)+(1.97*0.31)+(4.33*-0.45)+(4.51*-0.31)+\\(-4.08*-0.91)+(1.47*-0.31)+(-5.96*1.26)}}}{1+\exp^{\substack{-0.74+(-2.39*0.52)+(2.78*-0.33)+(-7.12*-0.53)+(-2.84*-0.21)+\\(-3.18*-0.10)+(5.86*-0.42)+(-3.47*-1.42)+(1.97*0.31)+(4.33*-0.45)+\\(4.51*-0.31)+(-4.08*-0.91)+(1.47*-0.31)+(-5.96*1.26)}}}$$

$$P_{severe} = 0.058$$

Since $P_{severe} < 0.5$ patient 429 is predicted to follow a mild disease course.

Similarly, for patient 483:

$$P_{severe} = \frac{\exp^{\substack{-0.74+(-2.39*-1.47)+(2.78*0.80)+(-7.12*-1.70)+(-2.84*-2.60)+(-3.18*-0.72)+\\(5.86*-0.54)+(-3.47*-0.67)+(1.97*-1.30)+(4.33*0.10)+(4.51*-1.18)+\\(-4.08*-1.62)+(1.47*-0.65)+(-5.96*0.55)}}}{1+\exp^{\substack{-0.74+(-2.39*-1.47)+(2.78*0.80)+(-7.12*-1.70)+(-2.84*-2.60)+\\(-3.18*-0.72)+(5.86*-0.54)+(-3.47*-0.67)+(1.97*-1.30)+(4.33*0.10)+\\(4.51*-1.18)+(-4.08*-1.62)+(1.47*-0.65)+(-5.96*0.55)}}}$$

$$P_{severe} = 1$$

Since $P_{severe} > 0.5$ patient 483 is predicted to follow a severe disease course (high risk of IBD progression).

14-gene Model

Rearranging equation (5) the probability of patient 429 following a severe disease course is given by:

$$P_{severe} = \frac{\exp^{\substack{0.04+(1.22*-0.33)+(-2.88*-0.53)+(-1.28*-0.85)+(-1.32*-0.1)+(1.51*-0.42)+\\(-1.6*-1.42)+(1.54*0.31)+(-1.14*-0.45)+(1.43*-0.31)+(-1.14*0.32)+\\(-1.03*-0.91)+(-1.35*2.34)+(1.71*-0.31)+(-2.25*1.26)}}}{1+\exp^{\substack{0.04+(1.22*-0.33)+(-2.88*-0.53)+(-1.28*-0.85)+(-1.32*-0.1)+\\(1.51*-0.42)+(-1.6*-1.42)+(1.54*0.31)+(-1.14*-0.45)+(1.43*-0.31)+\\(-1.14*0.32)+(-1.03*-0.91)+(-1.35*2.34)+(1.71*-0.31)+(-2.25*1.26)}}}$$

$$P_{severe} = 0.201$$

Since $P_{severe} < 0.5$ patient 429 is predicted to follow a mild disease course.

Similarly, for patient 483:

$$P_{severe} = \frac{\exp^{\substack{0.04+(1.22*0.80)+(-2.88*-1.70)+(-1.28*-0.88)+(-1.32*-0.72)+(1.51*-0.54)+\\(-1.6*-0.67)+(1.54*-1.30)+(-1.14*0.10)+(1.43*-1.18)+(-1.14*0.62)+\\(-1.03*-1.62)+(-1.35*-1.05)+(1.71*-0.65)+(-2.25*0.55)}}}{1+\exp^{\substack{0.04+(1.22*0.80)+(-2.88*-1.70)+(-1.28*-0.88)+(-1.32*-0.72)+\\(1.51*-0.54)+(-1.6*-0.67)+(1.54*-1.30)+(-1.14*0.10)+(1.43*-1.18)+\\(-1.14*0.62)+(-1.03*-1.62)+(-1.35*-1.05)+(1.71*-0.65)+(-2.25*0.55)}}}$$

$$P_{severe} = 0.98$$

Since $P_{severe} > 0.5$ patient 483 is predicted to follow a severe disease course (high risk of IBD progression).

16-gene Model

Rearranging equation (6) the probability of patient 429 following a severe disease course is given by:

$$P_{severe} = \frac{\exp^{\substack{0.81+(-3.13*0.52)+(5.56*-0.33)+(-9.38*-0.53)+(-2.86*-0.21)+(-3.25*-0.85)+\\(-5.12*-0.10)+(5.22*-0.428)+(-5.19*-1.42)+(4.17*0.31)+(5.97*-0.45)+\\(5.98*-0.31)+(-3.91*0.32)+(-2.73*-0.91)+(-1.85*2.34)+(3.89*-0.31)+\\(-6.83*1.26)}}}{1+\exp^{\substack{0.81+(-3.13*0.52)+(5.56*-0.33)+(-9.38*-0.53)+(-2.86*-0.21)+\\(-3.25*-0.85)+(-5.12*-0.10)+(5.22*-0.428)+(-5.19*-1.42)+(4.17*0.31)+\\(5.97*-0.45)+(5.98*-0.31)+(-3.91*0.32)+(-2.73*-0.91)+(-1.85*2.34)+\\(3.89*-0.31)+(-6.83*1.26)}}}$$

$$P_{severe} = 0.008$$

Since $P_{severe} < 0.5$ patient 429 is predicted to follow a mild disease course.

Similarly, for patient 483:

$$P_{severe} = \frac{\exp^{\substack{0.81+(-3.13*-1.47)+(5.56*0.80)+(-9.38*-1.70)+(-2.86*-2.60)+(-3.25*-0.88)+\\(-5.12*-0.72)+(5.22*-0.54)+(-5.19*-0.67)+(4.17*-1.30)+(5.97*0.10)+\\(5.98*-1.18)+(-3.91*0.62)+(-2.73*-1.62)+(-1.85*-1.05)+(3.89*-0.65)+\\(-6.83*0.55)}}}{1+\exp^{\substack{0.81+(-3.13*-1.47)+(5.56*0.80)+(-9.38*-1.70)+(-2.86*-2.60)+\\(-3.25*-0.88)+(-5.12*-0.72)+(5.22*-0.54)+(-5.19*-0.67)+(4.17*-1.30)+\\(5.97*0.10)+(5.98*-1.18)+(-3.91*0.62)+(-2.73*-1.62)+(-1.85*-1.05)+\\(3.89*-0.65)+(-6.83*0.55)}}}$$

$$P_{severe} = 1$$

Since $P_{severe} > 0.5$ patient 483 is predicted to follow a severe disease course.

The above, not limiting example, exemplifies one embodiment of the invention as applied to three, four, five, thirteen, fourteen, and 16 genes selected from the group consisting of ARRDC4, GBP5, P2RY14, VTRNA1-1, IL18RAP, HP, NUDT7, GZMH, TRGC2, GZMK, LGALSL, FCRL5, IFI44L, LINC01136, LY96, and TRGV3. However, the method can readily be adapted by those of skill in the art to two, three, four, five, six, seven, eight, nine, ten, eleven, twelve, thirteen, fourteen, fifteen, or sixteen genes selected from the group consisting of ARRDC4, GBP5, P2RY14, VTRNA1-1, IL18RAP, HP, NUDT7, GZMH, TRGC2, GZMK, LGALSL, FCRL5, IFI44L, LINC01136, LY96, and TRGV3.

Methods

RNA Extraction

A blood sample obtained from a subject is incubated in a PAXgene® tube (PAXgene Blood RNA Kit, Cat. No. 762164, BD Biosciences, San Jose, Calif.) at room temperature (15-25° C.) for 3 hours. The tube containing the sample is then centrifuged for 10 minutes at 4,000×g and the supernatant is decanted from the tube and discarded. Following decantation of the supernatant, the tube is closed using a fresh secondary BD Hemogard™ (PAXgene Blood RNA Kit, BD Biosciences, San Jose, Calif.) closure. The tube is then vortexed until the pellet is visibly dissolved and centrifuged for 10 minutes at 4,000×g. Following centrifugation, the entire supernatant is removed and discarded using a pipette. 350 µl of resuspension buffer BR1 (PAXgene Blood RNA Kit, BD Biosciences, San Jose, Calif.) is then added and the tube is vortexed until the pellet is visibly dissolved. The sample is then pipetted into a 1.5 ml microcentrifuge tube to which 300 µl of binding buffer BR2 (PAXgene Blood RNA MDx Kit, BD Biosciences, San Jose, Calif.) and 40 µl of proteinase K are individually added. The tube is then vortexed for 5 seconds and incubated for 10 minutes at 55° C. using a shaker-incubator at 1000 rpm. Following incubation, the lysate from the microcentrifuge tube is pipetted directly into a PAXgene® Shredder spin column (lilac) (PAXgene Blood RNA Kit, BD Biosciences, San Jose, Calif.) placed in a 2 ml processing tube and centrifuged for 3 minutes at 15,000×g. The entire supernatant of the flow-through fraction is then carefully pipetted to a fresh 1.5 ml microcentrifuge tube without disturbing the pellet in the processing tube. 350 µl of 96-100% ethanol is added to the supernatant, vortexed for 2 seconds, and centrifuged for 1 second at 500×g to remove drops from the inside of the tube lid. 700 µl of the sample is pipetted into the PAXgene® RNA spin column (red) (PAXgene Blood RNA Kit, BD Biosciences, San Jose, Calif.) placed in a 2 ml processing tube and centrifuged for 1 minute at 15,000×g. The spin column is placed in a new 2 ml processing tube and the old processing tube containing flow-through is discarded. The remaining sample is pipetted into a PAXgene® RNA spin column (PAXgene Blood RNA Kit, BD Biosciences, San Jose, Calif.) and centrifuged for 1 minute at 15,000×g. The spin column is placed in a new 2 ml processing tube and the old processing tube containing flow-through is discarded. 350 µl of wash buffer BR3 is pipetted into the PAXgene® RNA spin column and centrifuged for 1 minute at 15,000×g. The spin column is placed in a new 2 ml processing tube and the old processing tube containing flow-through is discarded.

In a separate 1.5 ml microcentrifuge tube, a DNase I incubation mix is made by mixing 10 µl of DNase I solution (PAXgene Blood RNA Kit, BD Biosciences, San Jose, Calif.) with 70 µl of buffer RDD (PAXgene Blood RNA Kit, BD Biosciences, San Jose, Calif.). 80 µl of the DNase I incubation mix is then added directly onto the PAXgene® RNA spin column membrane and incubated for 15 minutes at room temperature (20-30° C.). 350 µl of buffer BR3 is pipetted into the PAXgene® RNA spin column and centrifuged for 1 minute at 15,000×g. The spin column is placed in a new 2 ml processing tube and the old processing tube containing flow-through is discarded. 500 µl of wash buffer BR4 (PAXgene Blood RNA Kit, BD Biosciences, San Jose, Calif.) is pipetted into the PAXgene® RNA spin column and centrifuged for 1 minute at 15,000 g. The spin column is placed in a new 2 ml processing tube and the old processing tube containing flow-through is discarded. 500 µl of buffer BR4 is pipetted into the PAXgene® RNA spin column and centrifuged for 3 minutes at 15,000 g. The spin column is placed in a new 2 ml processing tube and centrifuged for 1 minute at 15,000×g. The PAXgene® RNA spin column is placed in a 1.5 ml microcentrifuge tube, 40 µl of elution buffer BR5 (PAXgene Blood RNA Kit, BD Biosciences, San Jose, Calif.) is pipetted directly onto the PAXgene RNA spin column membrane and centrifuged for 1 minute at 15,000×g to elute the RNA. Repeat the elution step using 40 µl of elution buffer BR5 and the same microcentrifuge tube. Incubate the eluate RNA sample at 65° C. for 5 minutes and immediately chill the RNA sample on ice.

RNA Quantification

Spin a ready to use aliquot of the Agilent RNA 6000 gel-dye mix tube (Agilent RNA 6000 Nano Kit, Cat. No. 5067-1511, Agilent, Santa Clara, Calif.) at 13,000×g for 10 minutes, and then allow the gel-dye mix to equilibrate at room temperature (15-25° C.) for 30 minutes. Place a new RNA Nano chip (Agilent RNA 6000 Nano Kit, Cat. No. 5067-1511, Agilent, Santa Clara, Calif.) onto a ready to use chip priming station (Cat. No. 5065-4401, Agilent, Santa Clara, Calif.). Pipette 9 µl of the gel-dye mix at the bottom of the well marked "G." In the chip priming station, position the plunger at 1 ml and close the chip priming station. Wait for exactly 30 seconds and then release the plunger with the clip release mechanism and visually inspect that the plunger moves back at least to the 0.3 ml mark. Wait for 5 seconds, then slowly pull back the plunger to the 1 ml position. Open the chip priming station and pipette 9 µl of the gel-dye mix in each of the reaction wells. Place a ready to use aliquot of the Agilent RNA 6000 Ladder (Cat. No. 5067-1529, Agilent, Santa Clara, Calif.) on ice for 15 minutes for complete thawing and then incubate at 70° C. for 2 minutes. Pipette 1 µl of the Agilent RNA 6000 Ladder into the well marked with the ladder symbol. Pipette 5 µl of the Agilent RNA 6000 Nano marker (Agilent RNA 6000 Nano Kit, Cat. No. 5067-1511, Agilent, Santa Clara, Calif.) into the well marked with the ladder symbol and each of the reaction wells. Pipette 1 µl of the RNA sample into the upper left well of the RNA Nano chip. Vortex the RNA Nano chip horizontally for 60 seconds at 2400 rpm. Place the chip carefully into the receptacle of the Agilent 2100 Bioanalyzer (Agilent, Santa Clara, Calif.) and close the lid and run the chip. Following completion of the run the integrity of the RNA is checked and if RIN>7 the RNA is quantified using a Nanodrop spectrophotometer prior to proceeding with cDNA synthesis.

cDNA Synthesis

In labeled 0.2 ml thin wall tube on ice combine the following to create a mix (Table 6):

TABLE 6

| Component | Number of patient samples to be analyzed (+Reference;+10%) | | | |
|---|---|---|---|---|
| | 1 | 2 | 3 | 4 |
| 5x VILO Reaction Mix (SuperScript ™ VILO ™ cDNA Synthesis Kit, Cat. No. 11754050, ThermoFisher Scientific, Grand Island, NY) | 15.4 µl | 19.8 µl | 24.2 µl | 28.6 µl |
| 10x SuperScript Enzyme Mix (SuperScript ™ VILO ™ cDNA Synthesis Kit, Cat. No. 11754050, ThermoFisher Scientific, Grand Island, NY) | 7.7 µl | 9.9 µl | 12.1 µl | 14.3 µl |
| Nuclease-free water | 15.4 µl | 19.8 µl | 24.2 µl | 28.6 µl |

For each sample, add 10 µl of the mix prepared in to 10 µl of the RNA sample diluted to 15 ng/µl (150 ng of RNA). For the Reference RNA, add 25 µl of the cDNA synthesis mix prepared in (2.) to 25 µl of the Reference RNA diluted to 15 ng/µl (375 ng). Gently mix and place tubes in a thermocycler (Eppendorf MasterCycler Nexus SX1, SKU #8125-30-1030, Eppendorf AG, Germany). Incubate at 25° C. for 10 minutes. Incubate at 42° C. for 60 minutes. Terminate reaction at 85° C. for 5 minutes. Let it cool to 4° C. Briefly centrifuge tube to collect contents at the bottom of the tube and store cDNA samples at −20° C. prior to qPCR.

qPCR

Resuspend the thawed cDNA samples vortexing gently, then centrifuge briefly to collect liquid at the bottom of the tube. For each sample, transfer contents to a labeled 0.5 ml tube and dilute 20× by adding 380 µl nuclease-free water. For the reference cDNA, transfer contents to a labeled 0.5 ml tube and dilute 5× by adding 200 µl nuclease-free water.

Depending on the number of cDNA samples to be analyzed, for each assay combine the following components in a labeled nuclease free 1.5 ml tube (Table 7):

TABLE 7

| PCR reaction mix component | Number of cDNA samples to be analyzed (+Reference +1) | | | |
|---|---|---|---|---|
|  | 1 | 2 | 3 | 4 |
| 20x Primer/Probe Mix (each primer at 50 micromolar, each probe at 10 micromolar) | 8 µl | 11 µl | 14 µl | 17 µl |
| 2x Taqman Gene Expression Master Mix ThermoFisher Scientific, Grand Island, NY) | 80 µl | 110 µl | 140 µl | 170 µl |
| Nuclease-free water | 40 µl | 55 µl | 70 µl | 85 µl |

The following exemplary RT-qPCR primers (Table 8) may be used. However, the skilled artisan is readily capable of designing other suitable primers to perform the presented exemplary RT-qPCR assay.

TABLE 8

| Gene | Forward primer | Reverse primer | Probe sequence |
|---|---|---|---|
| long intergenic non-protein coding RNA 1136 (LINC01136) | CCACATGATTTCCAGCTGAT (SEQ ID NO: 1) | CCAGGGCTTAGAGAGACCCT (SEQ ID NO: 2) | AGCAGAAATAGCTGTGGCAG (SEQ ID NO: 3) |
| nudix hydrolase 7 (NUDT7) | GTGGCTAAAGAAGGAAAACT (SEQ ID NO: 4) | CGCTTACCTCCAGGGAAGCA (SEQ ID NO: 5) | CATTTGTTGTTCACCGTCCG (SEQ ID NO: 6) |
| purinergic receptor P2Y14 (P2RY14) | GCGAATGGGAAAGGAGACCA (SEQ ID NO: 7) | GCCATGTCTCCAGAAGTAAA (SEQ ID NO: 8) | TTTCTTAGAAAGCAAATAAA (SEQ ID NO: 9) |
| interleukin 18 receptor accessory protein (IL18RAP) | CCTATTTCCTGATGTTTTAG (SEQ ID NO: 10) | TTGACATAGTTGGGGCTCAA (SEQ ID NO: 11) | AAACAAATATGGATATAGCC (SEQ ID NO: 12) |
| granzyme H (GZMH) | CTGAGAAAATGCAGCCATTC (SEQ ID NO: 13) | AGGCCATGTAGGGGCGGGAG (SEQ ID NO: 14) | TCCTCCTGTTGGCCTTTCTT (SEQ ID NO: 15) |
| interferon induced protein 44 like (IFI44L) | AATGTTGGCAAAAGTGAAGC (SEQ ID NO: 16) | CACTTTAGTAAGCAAGGCCA (SEQ ID NO: 17) | AGTTCACAAAGAAGTATTAA (SEQ ID NO: 18) |
| guanylate binding protein 5 (GBP5) | GGCAAAGTACTATCGGGAGC (SEQ ID NO: 19) | TCCTTGGACTTTAAATATTT (SEQ ID NO: 20) | TCGGAAAGGAATACAGGCTG (SEQ ID NO: 21) |
| Fc receptor like 5 (FCRL5) | AAATGTGGTTTACTCAGAAG (SEQ ID NO: 22) | TTCAGAGTAGATGATAGGGG (SEQ ID NO: 23) | ACGGATCATCCAAGAGAAAA (SEQ ID NO: 24) |
| lymphocyte antigen 96 (LY96) | TGAATACAACAATATCATTC (SEQ ID NO: 25) | AAGAGCATTTCTTCTGGGCT (SEQ ID NO: 26) | CCTTCAAGGGAATAAAATTT (SEQ ID NO: 27) |
| arrestin domain containing 4 (ARRDC4) | GCTGTCTTCTCGGAGGTGGA (SEQ ID NO: 28) | GATGGAAGTTGAAAGCGAAA (SEQ ID NO: 29) | TACCTGAACGTGCGCCTCAG (SEQ ID NO: 30) |
| Haptoglobin (HP) | TTTTGCAGTGGACTCAGGCA (SEQ ID NO: 31) | GTGCTCCACATAGCCATGTG (SEQ ID NO: 32) | TGATGTCACGGATATCGCAG (SEQ ID NO: 33) |
| vault RNA 1-1 (VTRNA1-1) | GGTTACTTCGACAGTTCTTT (SEQ ID NO: 34) | CGCCCGCGGGTCTCGAACAA (SEQ ID NO: 35) | ATTGAAACAAGCAACCTGTC (SEQ ID NO: 36) |

TABLE 8-continued

| Gene | Forward primer | Reverse primer | Probe sequence |
|---|---|---|---|
| T cell receptor gamma constant 2 (TRGC2) | CAAATGATGTCACCACAGTG (SEQ ID NO: 37) | CAGTAGTGTATCATTTGCAT (SEQ ID NO: 38) | ATCCCAAATACAATTATTCA (SEQ ID NO: 39) |
| lectin, galactosidase binding like (LGALSL) | GCAATCCCTTACTTTCCATT (SEQ ID NO: 40) | CCACAAACACTCGGAAACGT (SEQ ID NO: 41) | ATTCCAGACCAGCCATTCAG (SEQ ID NO: 42) |
| granzyme K (GZMK) | CTGTGCAGGAGATGCCAAAG (SEQ ID NO: 43) | AGACACCTTTACAGATCAAG (SEQ ID NO: 44) | CCAGAAGGATTCCTGTAAGG (SEQ ID NO: 45) |
| T cell receptor gamma variable 3 (TRGV3) | TTTCTATTTTAATGCCATAT (SEQ ID NO: 46) | TGATATGGACTTCTTTATGC (SEQ ID NO: 47) | TATATTTTCGTTCTGATATT (SEQ ID NO: 48) |
| CDV3 homolog (CDV3) (Reference) | GATTACAGCGGCCTCAGGGT (SEQ ID NO: 49) | GATCTTGTCTCTTTTCATTA (SEQ ID NO: 50) | CAGGCAATGCAAATAAGCAG (SEQ ID NO: 51) |
| RNA; 45S pre-ribosomal 5; RNA; 18S ribosomal 5 (RNA18S5) (Reference) | TGGTCGCTCGCTCCTCTCCT (SEQ ID NO: 52) | CGTCGGCATGTATTAGCTCT (SEQ ID NO: 53) | CTTGGATAACTGTGGTAATT (SEQ ID NO: 54) |

Cap the tube and invert several times to mix. Centrifuge briefly to collect the reaction mix in the bottom of the tube. The protocol below exemplifies an assay conducted on cDNA samples from four patients, measuring the expression levels of 16 genes along with two reference controls. However, the assay can be performed on one or more cDNA samples and can readily be designed by one of skill in the art to measure the expression levels of two or more genes of the 16 genes using one or more reference controls. Pipette 4 µl of each cDNA template into the wells of a labeled 384-well plate as follows:
   a. Reference cDNA (CDV3 and RNA85S5) wells A1-C6
   b. cDNA sample #1 wells D1-F6
   c. cDNA sample #2 wells G1-I6
   d. cDNA sample #3 wells J1-L6
   e. cDNA sample #4 wells M1-O6

Pipette 4 of nuclease-free water into each No Template Control well (wells P10P18).

Add 16 µl of each Taqman Gene Expression Assay into the following wells:
   a. Assay 1: Wells A1-A3, D1-D3, G1-G3, J1-J3, M1-M3, P1
   b. Assay 2: Wells A4-A6, D4-D6, G4-G6, J4-J6, M4-M6, P2
   c. Assay 3: Wells A7-A9, D7-D9, G7-G9, J7-J9, M7-M9, P3
   d. Assay 4: Wells A10-A12, D10-D12, G10-G12, J10-J12, M10-M12, P4
   e. Assay 5: Wells A13-A15, D13-D15, G13-G15, J13-J15, M13-M15, P5
   f. Assay 6: Wells A16-A18, D16-D18, G16-G18, J16-J18, M16-M18, P6
   g. Assay 7: Wells A19-A21, D19-D21, G19-G21, J19-J21, M19-M21, P7
   h. Assay 8: Wells A22-A24, D22-D24, G22-G24, J22-J24, M22-M24, P8
   i. Assay 9: Wells B1-B3, E1-E3, H1-H3, K1-K3, N1-N3, P9
   j. Assay 10: Wells B4-B6, E4-E6, H4-H6, K4-K6, N4-N6, P10
   k. Assay 11: Wells B7-B9, E7-E9, H7-H9, K7-K9, N7-N9, P11
   l. Assay 12: Wells B10-B12, E10-E12, H10-H12, K10-K12, N10-N12, P12
   m. Assay 13: Wells B13-B15, E13-E15, H13-H15, K13-K15, N13-N15, P13
   n. Assay 14: Wells B16-B18, E16-E18, H16-H18, K16-K18, N16-N18, P14
   o. Assay 15: Wells B19-B21, E19-E21, H19-H21, K19-K21, N19-N21, P15
   p. Assay 16: Wells B22-B24, E22-E24, H22-H24, K22-K24, N22-N24, P16
   q. Assay 17: Wells C1-C3, F1-F3, I1-I3, L1-L3, O1-O3, P17
   r. Assay 18: Wells C4-C6, F4-F6, I4-I6, L4-L6, O4-O6, P18

Seal the 384-well plate with the sealing foil (Cat. No. 04729757001, Roche Diagnostics Corporation, Indianapolis, Ind.). Centrifuge the plate briefly to mix the contents of the wells and load the plate into the thermocycler (Roche LightCycler480 II, Roche Diagnostics Corporation, Indianapolis, Ind.). Select detection format to Dual Color Hydrolysis Probe/UPL Probe, set the qPCR program as follows for 70 cycles, and run the assay:
   a. 95° C. for 10 minutes
   b. 95° C. for 10 seconds
   c. 60° C. for 1 minute
   d. 40° C. for 30 seconds.

REFERENCES

All documents mentioned in this specification are incorporated herein by reference in their entirety.

Ananthakrishnan, Ashwin N., et al. "Differential effect of genetic burden on disease phenotypes in Crohn's disease and ulcerative colitis: analysis of a North American cohort." *The American journal of gastroenterology* 109.3 (2014): 395.

Billiet, Thomas, Marc Ferrante, and Gert Van Assche. "The use of prognostic factors in inflammatory bowel diseases." *Current gastroenterology reports* 16.11 (2014): 1-14.

Bolstad, Benjamin Milo. "preprocessCore: A collection of pre-processing functions." *R package version* 1.0 (2013).

Choi, Jung Kyoon, and Sang Cheol Kim. "Environmental effects on gene expression phenotype have regional biases in the human genome." *Genetics* 175.4 (2007): 1607-1613.

Colombel, Jean Frederic, et al. "Infliximnab, azathioprine, or combination therapy for Crohn's disease." New England Journal of Medicine 362.15 (2010): 1383-1395.

D'Haens, Geert, et al. "Early combined immunosuppression or conventional management in patients with newly diagnosed Crohn's disease: an open randomised trial." The Lancet 371.9613 (2008): 660-667.

Freeman, Willard M., Stephen J. Walker, and Kent E. Vrana. "Quantitative RT-PCR: pitfalls and potential." *Biotechniques* 26 (1999): 112-125.

Friedman, David J., Laurence A. Turka, and Simon C. Robson. "There's a goat behind door number 3: from Monty Hall to medicine." *The Journal of clinical investigation* 121.10 (2011): 3819.

Gerich, Mark E., and Dermot P B McGovern. "Towards personalized care in IBD." *Nature Reviews Gastroenterology & Hepatology* 11.5 (2014): 287-299.

Huber, Wolfgang, et al. "Orchestrating high-throughput genomic analysis with Bioconductor." *Nature methods* 12.2 (2015): 115-121.

IBD Research Priority, Setting Partnership (2015). Inflammatory Bowel Disease (IBD) Research Priorities. Accessed: 2015-04-20. url: http://www.bsg.org. uk/images/stories/docs/research/ibd_psp_top10_final.pdf.

Jess, Tine, et al. "Changes in clinical characteristics, course, and prognosis of inflammatory bowel disease during the last 5 decades: a population-based study from Copenhagen, Denmark." *Inflammatory bowel diseases* 13.4 (2007): 481-489.

Jostins, Luke, et al. "Host-microbe interactions have shaped the genetic architecture of inflammatory bowel disease." *Nature* 491.7422 (2012): 119-124.

Kaser, A, S Zeissig, and R S Blumberg (2010). "Inflammatory Bowel Disease". In: Annual Review of Immunology 28, pp. 573-621.

Lee, James C., et al. "Gene expression profiling of CD8+ T cells predicts prognosis in patients with Crohn disease and ulcerative colitis." *The Journal of clinical investigation* 121.10 (2011): 4170-4179.

Livak, Kenneth J., and Thomas D. Schmittgen. "Analysis of relative gene expression data using real-time quantitative PCR and the 2-ΔΔCT nnethod."methods 25.4 (2001): 402-408.

Loly, Catherine, Jacques Belaiche, and Edouard Louis. "Predictors of severe Crohn's disease." *Scandinavian journal of gastroenterology* 43.8 (2008): 948-954.

Lyons, Paul A., et al. "Novel expression signatures identified by transcriptional analysis of separated leucocyte subsets in systemic lupus erythematosus and vasculitis." *Annals of the rheumatic diseases* 69.6 (2010): 1208-1213.

Lyons, Paul A., et al. "Microarray analysis of human leucocyte subsets: the advantages of positive selection and rapid purification." BMC genomics 8.1 (2007): 1.

Markowitz, James, et al. "The Prometheus Crohn's prognostic test does not reliably predict complicated Crohn's disease in children." *Gastroenterology* 140.5 (2011): S-153.

McKinney, Eoin F., et al. "A CD8+ T cell transcription signature predicts prognosis in autoimmune disease." *Nature medicine* 16.5 (2010): 586-591.

McKinney, Eoin F., et al. "T-cell exhaustion, co-stimulation and clinical outcome in autoimmunity and infection." *Nature* (2015).

Micheel, Christine M., Sharly J. Nass, and Gilbert S. Omenn, eds. *Evolution of translational omics: lessons learned and the path forward.* National Academies Press, 2012.

Peyrin-Biroulet, Laurent, et al. "Surgery in a population-based cohort of Crohn's disease from Olmsted County, Minnesota (1970-2004)." *The American journal of gastroenterology* 107.11 (2012): 1693-1701.

Schena, Mark, et al. "Quantitative monitoring of gene expression patterns with a complementary DNA microarray." *Science* 270.5235 (1995): 467.

---

The invention claimed is:

1. A method of quantifying gene expression products on an array of patient-identified selected gene expression products from a patient who has presented for inflammatory bowel disease (IBD), the method comprising the steps of:
   a) providing RNA from a whole blood sample of said patient;
   b) converting said RNA into cDNA;
   c) placing individual aliquots of said cDNA on an array;
   d) performing RT-qPCR, digital PCR, or sequencing on said individual cDNA aliquots for each of three or more genes selected from the group consisting essentially of: ARRDC4, GBP5, P2RY14, VTRNA1-1, IL18RAP, HP, NUDT7, GZMH, TRGC2, GZMK, LGALSL, FCRL5, IFI44L, LINC01136, LY96, and TRGV3 so as to provide RT-qPCR, digital PCR or sequencing products on said array, thereby providing said array of patient-identified selected gene expression products consisting essentially of said three or more gene expression products;
e) quantifying the amount of a gene expression product for each selected gene of said three or more genes relative to a control for each selected gene, wherein said control for each selected gene is the median expression level of gene expression product of said gene in a group of patients who have been diagnosed with IBD progression;

wherein for each selected gene expression product on said array, the amount of gene expression product for a gene selected from the group consisting essentially of: ARRDC4, GBP5, P2RY14, VTRNA1-1, IL18RAP, HP, NUDT7, GZMH, TRGC2, and GZMK, is lower than a said control for said gene; and the amount of gene expression product for a gene selected from the group consisting essentially of: LGALSL, FCRL5, IFI44L, LINC01136, LY96, and TRGV3 is higher than said control for said gene.

2. The method of claim 1, further comprising the step of (e) quantifying said RT-qPCR, digital PCR or sequencing products.

3. The method of claim 1, wherein said RT-qPCR product is provided by contacting said cDNA with a primer set specific for each of said three or more genes.

4. The method of claim 3, wherein said primer set comprises a forward primer, a reverse primer, and a probe.

5. The method of claim 1, wherein four, five, thirteen, fourteen, or sixteen of said genes are selected from the group consisting of ARRDC4, GBP5, P2RY14, VTRNA1-1, IL18RAP, HP, NUDT7, GZMH, TRGC2, GZMK, LGALSL, FCRL5, IFI44L, LINC01136, LY96, and TRGV3.

6. The method of claim 1, wherein said group of patients who have been diagnosed with IBD progression experienced one or more indicators selected from the group consisting of:

an average of 0.5 or greater relapses over a period of 12 months after initial presentation of the disease;
more treatment escalations per unit time of follow up compared to patients in the IBD2 group; and
a more frequent or more aggressive disease treatment regimen than the treatment normally administered during the maintenance phase of IBD.

7. The method of claim 1, said group of patients comprising 10 patients who had IBD progression.

8. The method of claim 1, said group of patients comprising 100 patients who had IBD progression.

9. The method of claim 1, wherein the three or more genes are selected from the group consisting of: ARRDC4, GBP5, P2RY14, VTRNA1-1, IL18RAP, HP, NUDT7, GZMH, TRGC2, GZMK, LGALSL, FCRL5, IFI44L, LINC01136, LY96, and TRGV3.

10. A method of quantifying gene expression products on an array of patient-identified selected gene expression products from a patient who has presented for inflammatory bowel disease (IBD), the method comprising the steps of:
a) providing RNA from a whole blood sample of said patient;
b) converting said RNA into cDNA;
c) placing individual aliquots of said cDNA on an array;
d) performing RT-qPCR, digital PCR, or sequencing on said individual cDNA aliquots for each of three or more genes selected from the group consisting essentially of: ARRDC4, GBP5, P2RY14, VTRNA1-1, IL18RAP, HP, NUDT7, GZMH, TRGC2, GZMK, LGALSL, FCRL5, IFI44L, LINC01136, LY96, and TRGV3 so as to provide RT-qPCR, digital PCR or sequencing products on said array, thereby providing said array of patient-identified selected gene expression products consisting essentially of said three or more gene expression products;
e) quantifying the amount of a gene expression product for each selected gene of said three or more genes relative to a control for each selected gene, wherein said control for each selected gene is the median expression level of gene expression product of said gene in a group of patients who have been diagnosed with IBD progression;

wherein for each selected gene expression product on said array, the amount of gene expression product for a gene selected from the group consisting essentially of: ARRDC4, GBP5, P2RY14, VTRNA1-1, IL18RAP, HP, NUDT7, GZMH, TRGC2, and GZMK, is higher than said control for said gene; and the amount of gene expression product for a gene selected from the group consisting essentially of: LGALSL, FCRL5, IFI44L, LINC01136, LY96, and TRGV3 is lower than said control for said gene.

11. The method of claim 10, further comprising the step of (e) quantifying said RT-qPCR, digital PCR or sequencing products.

12. The method of claim 10, wherein said RT-qPCR product is provided by contacting said cDNA with a primer set specific for each of said three or more genes.

13. The method of claim 12, wherein said primer set comprises a forward primer, a reverse primer, and a probe.

14. The method of claim 10, wherein said group of patients who have been diagnosed with IBD progression experienced one or more indicators selected from the group consisting of:

an average of 0.5 or greater relapses over a period of 12 months after initial presentation of the disease;
more treatment escalations per unit time of follow up compared to patients in the IBD2 group; and
a more frequent or more aggressive disease treatment regimen than the treatment normally administered during the maintenance phase of IBD.

15. The method of claim 10, said group of patients comprising 10 patients who had IBD progression.

16. The method of claim 10, said group of patients comprising 100 patients who had IBD progression.

17. The method of claim 10, wherein four, five, thirteen, fourteen, or sixteen of said genes are selected from the group consisting of ARRDC4, GBP5, P2RY14, VTRNA1-1, IL18RAP, HP, NUDT7, GZMH, TRGC2, GZMK, LGALSL, FCRL5, IFI44L, LINC01136, LY96, and TRGV3.

18. The method of claim 10, wherein the three or more genes are selected from the group consisting of: ARRDC4, GBP5, P2RY14, VTRNA1-1, IL18RAP, HP, NUDT7, GZMH, TRGC2, GZMK, LGALSL, FCRL5, IFI44L, LINC01136, LY96, and TRGV3.

19. The method of claim 1, wherein said sequencing comprises whole transcriptome shotgun sequencing.

20. The method of claim 10, wherein said sequencing comprises whole transcriptome shotgun sequencing.

* * * * *

SEQUENCE LISTING

<160> NUMBER OF SEQ ID NOS: 54

<210> SEQ ID NO 1
<211> LENGTH: 20
<212> TYPE: DNA
<213> ORGANISM: artificial
<220> FEATURE:
<223> OTHER INFORMATION: forward primer

<400> SEQUENCE: 1
ccacatgatt tccagctgat                                               20

<210> SEQ ID NO 2
<211> LENGTH: 20
<212> TYPE: DNA
<213> ORGANISM: artificial
<220> FEATURE:
<223> OTHER INFORMATION: reverse primer

<400> SEQUENCE: 2
ccagggctta gagagaccct                                               20

<210> SEQ ID NO 3

```
<211> LENGTH: 20
<212> TYPE: DNA
<213> ORGANISM: artificial
<220> FEATURE:
<223> OTHER INFORMATION: probe

<400> SEQUENCE: 3
agcagaaata gctgtggcag                                               20

<210> SEQ ID NO 4
<211> LENGTH: 20
<212> TYPE: DNA
<213> ORGANISM: artificial
<220> FEATURE:
<223> OTHER INFORMATION: forward primer

<400> SEQUENCE: 4
gtggctaaag aaggaaaact                                               20

<210> SEQ ID NO 5
<211> LENGTH: 20
<212> TYPE: DNA
<213> ORGANISM: artificial
<220> FEATURE:
<223> OTHER INFORMATION: reverse primer

<400> SEQUENCE: 5
cgcttacctc cagggaagca                                               20

<210> SEQ ID NO 6
<211> LENGTH: 20
<212> TYPE: DNA
<213> ORGANISM: artificial
<220> FEATURE:
<223> OTHER INFORMATION: probe

<400> SEQUENCE: 6
catttgttgt tcaccgtccg                                               20

<210> SEQ ID NO 7
<211> LENGTH: 20
<212> TYPE: DNA
<213> ORGANISM: artificial
<220> FEATURE:
<223> OTHER INFORMATION: forward primer

<400> SEQUENCE: 7
gcgaatggga aaggagacca                                               20

<210> SEQ ID NO 8
<211> LENGTH: 20
<212> TYPE: DNA
<213> ORGANISM: artificial
<220> FEATURE:
<223> OTHER INFORMATION: reverse primer

<400> SEQUENCE: 8
gccatgtctc cagaagtaaa                                               20

<210> SEQ ID NO 9
<211> LENGTH: 20
<212> TYPE: DNA
<213> ORGANISM: artificial
<220> FEATURE:
<223> OTHER INFORMATION: probe

<400> SEQUENCE: 9
```
tttcttagaa agcaaataaa                                              20

<210> SEQ ID NO 10
<211> LENGTH: 20
<212> TYPE: DNA
<213> ORGANISM: artificial
<220> FEATURE:
<223> OTHER INFORMATION: forward primer

<400> SEQUENCE: 10
cctatttcct gatgttttag                                              20

<210> SEQ ID NO 11
<211> LENGTH: 20
<212> TYPE: DNA
<213> ORGANISM: artificial
<220> FEATURE:
<223> OTHER INFORMATION: reverse primer

<400> SEQUENCE: 11
ttgacatagt tggggctcaa                                              20

<210> SEQ ID NO 12
<211> LENGTH: 20
<212> TYPE: DNA
<213> ORGANISM: artificial
<220> FEATURE:
<223> OTHER INFORMATION: probe

<400> SEQUENCE: 12
aaacaaatat ggatatagcc                                              20

<210> SEQ ID NO 13
<211> LENGTH: 20
<212> TYPE: DNA
<213> ORGANISM: artificial
<220> FEATURE:
<223> OTHER INFORMATION: forward primer

<400> SEQUENCE: 13
ctgagaaaat gcagccattc                                              20

<210> SEQ ID NO 14
<211> LENGTH: 20
<212> TYPE: DNA
<213> ORGANISM: artificial
<220> FEATURE:
<223> OTHER INFORMATION: reverse primer

<400> SEQUENCE: 14
aggccatgta ggggcgggag                                              20

<210> SEQ ID NO 15
<211> LENGTH: 20
<212> TYPE: DNA
<213> ORGANISM: artificial
<220> FEATURE:
<223> OTHER INFORMATION: probe

<400> SEQUENCE: 15
tcctcctgtt ggcctttctt                                              20

<210> SEQ ID NO 16
<211> LENGTH: 20
<212> TYPE: DNA

```
<213> ORGANISM: artificial
<220> FEATURE:
<223> OTHER INFORMATION: forward primer

<400> SEQUENCE: 16
aatgttggca aaagtgaagc                                              20

<210> SEQ ID NO 17
<211> LENGTH: 20
<212> TYPE: DNA
<213> ORGANISM: artificial
<220> FEATURE:
<223> OTHER INFORMATION: reverse primer

<400> SEQUENCE: 17
cactttagta agcaaggcca                                              20

<210> SEQ ID NO 18
<211> LENGTH: 20
<212> TYPE: DNA
<213> ORGANISM: artificial
<220> FEATURE:
<223> OTHER INFORMATION: probe

<400> SEQUENCE: 18
agttcacaaa gaagtattaa                                              20

<210> SEQ ID NO 19
<211> LENGTH: 20
<212> TYPE: DNA
<213> ORGANISM: artificial
<220> FEATURE:
<223> OTHER INFORMATION: forward primer

<400> SEQUENCE: 19
ggcaaagtac tatcgggagc                                              20

<210> SEQ ID NO 20
<211> LENGTH: 20
<212> TYPE: DNA
<213> ORGANISM: artificial
<220> FEATURE:
<223> OTHER INFORMATION: reverse primer

<400> SEQUENCE: 20
tccttggact ttaaatattt                                              20

<210> SEQ ID NO 21
<211> LENGTH: 20
<212> TYPE: DNA
<213> ORGANISM: artificial
<220> FEATURE:
<223> OTHER INFORMATION: probe

<400> SEQUENCE: 21
tcggaaagga atacaggctg                                              20

<210> SEQ ID NO 22
<211> LENGTH: 20
<212> TYPE: DNA
<213> ORGANISM: artificial
<220> FEATURE:
<223> OTHER INFORMATION: forward primer

<400> SEQUENCE: 22
aaatgtggtt tactcagaag                                              20
```

<210> SEQ ID NO 23
<211> LENGTH: 20
<212> TYPE: DNA
<213> ORGANISM: artificial
<220> FEATURE:
<223> OTHER INFORMATION: reverse primer

<400> SEQUENCE: 23
ttcagagtag atgatagggg                                            20

<210> SEQ ID NO 24
<211> LENGTH: 20
<212> TYPE: DNA
<213> ORGANISM: artificial
<220> FEATURE:
<223> OTHER INFORMATION: probe

<400> SEQUENCE: 24
acggatcatc caagagaaaa                                            20

<210> SEQ ID NO 25
<211> LENGTH: 20
<212> TYPE: DNA
<213> ORGANISM: artificial
<220> FEATURE:
<223> OTHER INFORMATION: forward primer

<400> SEQUENCE: 25
tgaatacaac aatatcattc                                            20

<210> SEQ ID NO 26
<211> LENGTH: 20
<212> TYPE: DNA
<213> ORGANISM: artificial
<220> FEATURE:
<223> OTHER INFORMATION: reverse primer

<400> SEQUENCE: 26
aagagcattt cttctgggct                                            20

<210> SEQ ID NO 27
<211> LENGTH: 20
<212> TYPE: DNA
<213> ORGANISM: artificial
<220> FEATURE:
<223> OTHER INFORMATION: probe

<400> SEQUENCE: 27
ccttcaaggg aataaaattt                                            20

<210> SEQ ID NO 28
<211> LENGTH: 20
<212> TYPE: DNA
<213> ORGANISM: artificial
<220> FEATURE:
<223> OTHER INFORMATION: forward primer

<400> SEQUENCE: 28
gctgtcttct cggaggtgga                                            20

<210> SEQ ID NO 29
<211> LENGTH: 20
<212> TYPE: DNA
<213> ORGANISM: artificial
<220> FEATURE:

<223> OTHER INFORMATION: reverse primer

<400> SEQUENCE: 29
gatggaagtt gaaagcgaaa					20

<210> SEQ ID NO 30
<211> LENGTH: 20
<212> TYPE: DNA
<213> ORGANISM: artificial
<220> FEATURE:
<223> OTHER INFORMATION: probe

<400> SEQUENCE: 30
tacctgaacg tgcgcctcag					20

<210> SEQ ID NO 31
<211> LENGTH: 20
<212> TYPE: DNA
<213> ORGANISM: artificial
<220> FEATURE:
<223> OTHER INFORMATION: forward primer

<400> SEQUENCE: 31
ttttgcagtg gactcaggca					20

<210> SEQ ID NO 32
<211> LENGTH: 20
<212> TYPE: DNA
<213> ORGANISM: artificial
<220> FEATURE:
<223> OTHER INFORMATION: reverse primer

<400> SEQUENCE: 32
gtgctccaca tagccatgtg					20

<210> SEQ ID NO 33
<211> LENGTH: 20
<212> TYPE: DNA
<213> ORGANISM: artificial
<220> FEATURE:
<223> OTHER INFORMATION: probe

<400> SEQUENCE: 33
tgatgtcacg gatatcgcag					20

<210> SEQ ID NO 34
<211> LENGTH: 20
<212> TYPE: DNA
<213> ORGANISM: artificial
<220> FEATURE:
<223> OTHER INFORMATION: forward primer

<400> SEQUENCE: 34
ggttacttcg acagttcttt					20

<210> SEQ ID NO 35
<211> LENGTH: 20
<212> TYPE: DNA
<213> ORGANISM: artificial
<220> FEATURE:
<223> OTHER INFORMATION: reverse primer

<400> SEQUENCE: 35
cgcccgcggg tctcgaacaa					20

```
<210> SEQ ID NO 36
<211> LENGTH: 20
<212> TYPE: DNA
<213> ORGANISM: artificial
<220> FEATURE:
<223> OTHER INFORMATION: probe

<400> SEQUENCE: 36
attgaaacaa gcaacctgtc                                               20

<210> SEQ ID NO 37
<211> LENGTH: 20
<212> TYPE: DNA
<213> ORGANISM: artificial
<220> FEATURE:
<223> OTHER INFORMATION: forward primer

<400> SEQUENCE: 37
caaatgatgt caccacagtg                                               20

<210> SEQ ID NO 38
<211> LENGTH: 20
<212> TYPE: DNA
<213> ORGANISM: artificial
<220> FEATURE:
<223> OTHER INFORMATION: reverse primer

<400> SEQUENCE: 38
cagtagtgta tcatttgcat                                               20

<210> SEQ ID NO 39
<211> LENGTH: 20
<212> TYPE: DNA
<213> ORGANISM: artificial
<220> FEATURE:
<223> OTHER INFORMATION: probe

<400> SEQUENCE: 39
atcccaaata caattattca                                               20

<210> SEQ ID NO 40
<211> LENGTH: 20
<212> TYPE: DNA
<213> ORGANISM: artificial
<220> FEATURE:
<223> OTHER INFORMATION: forward primer

<400> SEQUENCE: 40
gcaatccctt actttccatt                                               20

<210> SEQ ID NO 41
<211> LENGTH: 20
<212> TYPE: DNA
<213> ORGANISM: artificial
<220> FEATURE:
<223> OTHER INFORMATION: reverse primer

<400> SEQUENCE: 41
ccacaaacac tcggaaacgt                                               20

<210> SEQ ID NO 42
<211> LENGTH: 20
<212> TYPE: DNA
<213> ORGANISM: artificial
<220> FEATURE:
<223> OTHER INFORMATION: probe
```

<400> SEQUENCE: 42
attccagacc agccattcag                                                                20

<210> SEQ ID NO 43
<211> LENGTH: 20
<212> TYPE: DNA
<213> ORGANISM: artificial
<220> FEATURE:
<223> OTHER INFORMATION: forward primer

<400> SEQUENCE: 43
ctgtgcagga gatgccaaag                                                                20

<210> SEQ ID NO 44
<211> LENGTH: 20
<212> TYPE: DNA
<213> ORGANISM: artificial
<220> FEATURE:
<223> OTHER INFORMATION: reverse primer

<400> SEQUENCE: 44
agacaccttt acagatcaag                                                                20

<210> SEQ ID NO 45
<211> LENGTH: 20
<212> TYPE: DNA
<213> ORGANISM: artificial
<220> FEATURE:
<223> OTHER INFORMATION: probe

<400> SEQUENCE: 45
ccagaaggat tcctgtaagg                                                                20

<210> SEQ ID NO 46
<211> LENGTH: 20
<212> TYPE: DNA
<213> ORGANISM: artificial
<220> FEATURE:
<223> OTHER INFORMATION: forward primer

<400> SEQUENCE: 46
tttctatttt aatgccatat                                                                20

<210> SEQ ID NO 47
<211> LENGTH: 20
<212> TYPE: DNA
<213> ORGANISM: artificial
<220> FEATURE:
<223> OTHER INFORMATION: reverse primer

<400> SEQUENCE: 47
tgatatggac ttctttatgc                                                                20

<210> SEQ ID NO 48
<211> LENGTH: 20
<212> TYPE: DNA
<213> ORGANISM: artificial
<220> FEATURE:
<223> OTHER INFORMATION: probe

<400> SEQUENCE: 48
tatattttcg ttctgatatt                                                                20

<210> SEQ ID NO 49
<211> LENGTH: 20

```
<212> TYPE: DNA
<213> ORGANISM: artificial
<220> FEATURE:
<223> OTHER INFORMATION: forward primer

<400> SEQUENCE: 49
gattacagcg gcctcagggt                                          20

<210> SEQ ID NO 50
<211> LENGTH: 20
<212> TYPE: DNA
<213> ORGANISM: artificial
<220> FEATURE:
<223> OTHER INFORMATION: reverse primer

<400> SEQUENCE: 50
gatcttgtct cttttcatta                                          20

<210> SEQ ID NO 51
<211> LENGTH: 20
<212> TYPE: DNA
<213> ORGANISM: artificial
<220> FEATURE:
<223> OTHER INFORMATION: probe

<400> SEQUENCE: 51
caggcaatgc aaataagcag                                          20

<210> SEQ ID NO 52
<211> LENGTH: 20
<212> TYPE: DNA
<213> ORGANISM: artificial
<220> FEATURE:
<223> OTHER INFORMATION: forward primer

<400> SEQUENCE: 52
tggtcgctcg ctcctctcct                                          20

<210> SEQ ID NO 53
<211> LENGTH: 20
<212> TYPE: DNA
<213> ORGANISM: artificial
<220> FEATURE:
<223> OTHER INFORMATION: reverse primer

<400> SEQUENCE: 53
cgtcggcatg tattagctct                                          20

<210> SEQ ID NO 54
<211> LENGTH: 20
<212> TYPE: DNA
<213> ORGANISM: artificial
<220> FEATURE:
<223> OTHER INFORMATION: probe

<400> SEQUENCE: 54
cttggataac tgtggtaatt                                          20
```